US010888568B2

(12) United States Patent
Huang et al.

(10) Patent No.: US 10,888,568 B2
(45) Date of Patent: Jan. 12, 2021

(54) PHARMACEUTICAL COMPOSITION FOR TREATMENT OF CANCER USING PHENOTHIAZINE

(71) Applicants: Chi-Ying Huang, Taipei (TW); Jane Hsiao, Miami, FL (US); Pan-Chyr Yang, Taipei (TW); Meng-Hua Lee, Taipei (TW)

(72) Inventors: Chi-Ying Huang, Taipei (TW); Jane Hsiao, Miami, FL (US); Pan-Chyr Yang, Taipei (TW); Meng-Hua Lee, Taipei (TW)

(73) Assignee: National Yang Ming University, Taipei (TW)

( * ) Notice: Subject to any disclaimer, the term of this patent is extended or adjusted under 35 U.S.C. 154(b) by 0 days.

(21) Appl. No.: 16/172,888

(22) Filed: Oct. 29, 2018

(65) Prior Publication Data
US 2019/0070191 A1 Mar. 7, 2019

Related U.S. Application Data

(63) Continuation of application No. 14/841,727, filed on Sep. 1, 2015, which is a continuation-in-part of application No. 14/354,873, filed on Apr. 28, 2014, now abandoned.

(60) Provisional application No. 62/044,432, filed on Sep. 2, 2014.

(51) Int. Cl.
*A61K 31/5415* (2006.01)
*A61K 31/549* (2006.01)
*A61K 31/519* (2006.01)
*A61K 31/555* (2006.01)
*A61K 31/7068* (2006.01)
*A61K 31/5377* (2006.01)
*A61K 33/24* (2019.01)

(52) U.S. Cl.
CPC ........ *A61K 31/5415* (2013.01); *A61K 31/519* (2013.01); *A61K 31/5377* (2013.01); *A61K 31/549* (2013.01); *A61K 31/555* (2013.01); *A61K 31/7068* (2013.01); *A61K 33/24* (2013.01)

(58) Field of Classification Search
None
See application file for complete search history.

(56) References Cited

U.S. PATENT DOCUMENTS

| 7,250,891 | B2 | 7/2007 | Nishimura | |
| 2005/0137185 | A1* | 6/2005 | Lee | A61K 45/06 514/217 |
| 2012/0309799 | A1* | 12/2012 | Kim | C07C 279/26 514/357 |

FOREIGN PATENT DOCUMENTS

| CN | 1552328 | | 12/2004 |
| GB | 873316 A | | 7/1961 |
| WO | WO2013/033688 | * | 3/2013 |

OTHER PUBLICATIONS

Csonka et al. (In vivo 27: 815-820, 2013).*
Patrick et al. (CHIRALITY 3:208-211, 1991).*
Wrangari-Talbot et al. (J Can Res Updates. Oct. 31, 2013; 2(4): 265-282).*
Park et al., Predicted Drug-Induced Bradycardia Related Cardio Toxicity Using a Zebrafish in vivo Model, Nov. 5, 2012, Toxicology Letters 216(2013) 9-15, Elsevier, Ireland.
Shiotani et al., Practical Application of Guinea Pig Telemetry System for QT Evaluation, May 2, 2005, The Journal of Toxicological Sciences 30:3 239-247, Japanese Soc. Tox, Japan.
Kim et al., The Phenothiazine Drugs Inhibit hERG Potassium Channels, Drug and Chemical Toxicology, 28:303-313(2005), Taylor & Francis Inc., UK.
Kennerly et al.,Relative Configuration of Thioridazine Enantiomers, Mar. 1, 1991, Chirality 3:208-211 (1991), Wiley-Liss, Inc., US.
Park et al., Thioridazine Inhibits Angiogenesis and Tumor Growth, Jun. 6, 2014, Oncotarget 5:13 4929-34, Impact Journals, US.
Lang et al., Effect of Thioridazine on Erythrocytes, Oct. 23, 2013, Toxins 2013:5 1918-31, MDPI, Basel, Switzerland.
Chigaev et al., Is Prolonged Stem Cell Mobilization Detrimental for Hematopoiesis, Dec. 1, 2011, Med Hypotheses. 77(6): 1111-1113, NIH Public Access, US.
Min et. al., Antipsychotic Agent Thoirdazine Sensitizes Renal Carcinoma Caki Cells, Feb. 20, 2014, Cell Death and Disease (2014) 5:1063, Macmillian Publishers Ltd, US.
Lu et. al., Roles of Dopamine Receptors and Their Antagonis Thioridazine in Hepatoma Metastasis, Jun. 22, 2015, OncoTargets and Therapy 2015:8 1543-1552, Dove Press, UK.
Hale et al. Cardiotoxicity of Thioridazine and Two Stereoisomeric Forms of Thioridazine 5-Sulfoxide, Jun. 19, 1986,Toxicology and Applied Pharmacology 86-44-55 (1986), Elsevier,US.
Kilts et al., Effects of Thioridazine and its Metabolites on Dopaminergic Function, Aug. 13, 1984, The Journal of Pharmacology and Experimental Therapeutics 231:2 334, ASPET, US.
Su et al., Mesoridazine: An Open-Channel Blocker of Human Ether, Oct. 30, 2003, Journal of Molecular and Cellular Cardiology, 36 (2004) 151-160, Elsevier, US.

(Continued)

*Primary Examiner* — Bong-Sook Baek

(57) ABSTRACT

The present invention relates to use of antipsychotic phenothiazine derivative for treatment of cancer. The invention also provides a use for manufacture a medicament, a pharmaceutical composition and a method for treating a cancer, and/or preventing or delaying cancer recurrence based on trifluoperazine. The invention further provides a use for manufacture a medicament, a pharmaceutical composition and a method for treating cancer based on thioridazine and its enantiomers. Additionally, the invention provides a use for manufacture a medicament, a pharmaceutical composition and a method for treating KRAS mutant NSCLC comprising thioridazine.

10 Claims, 28 Drawing Sheets

(56) References Cited

OTHER PUBLICATIONS

Svendsen et al. Receptor Affinity, Neurochemistry and Behavioal Characterstics of the Enantiomers of Thiordazine, Apr. 22, 1988, Neuropharmacology 7:11 1117-1124, Pergamon PressUK.
U.S. Appl. No. 14/461,783, filed Feb. 5, 2015, Bhatia et al.
U.S. Appl. No. 12/612,054, filed May 6, 2010, Gant et al.

* cited by examiner

FIG 18

| Compound Name | (μM) | (μM) | Yes/No |
|---|---|---|---|
| | >10 | 1.25~2.5 | Yes |
| | >10 | 5~10 | No |
| | >10 | 2.5~5 | Yes |
| | 5~10 | 2.5~5 | Yes |
| | >10 | ND | No |
| | >10 | 1~2.5 | No |
| | >10 | 5~10 | No |
| | >10 | 5~10 | Yes |
| | >10 | ND | Yes |
| | >10 | ND | Yes |

ND: not determined. MTT and clonogenic assays were performed for A549 cells, whereas the side population data were from experiments conducted on CL141 cells.

FIG 19

| Cell line | Gender | Histology | clinical information | EGFR mutation status | PTEN mutation status | p53 mutation status | KRAS mutation status | Resistance to EGFR-TKI | IC50 for gefitinib | IC50 for trifluoperazine |
|---|---|---|---|---|---|---|---|---|---|---|
| CL83 | Male | adenocarcinoma | Collected on the 16th day after gefitinib treatment, disease progression | WT | Normal | ND | WT | intrinsic resistance | >10 µM | 14 µM |
| CL141 | Male | adenocarcinoma | Collected while chemonaive | WT | Loss | R248W | WT | intrinsic resistance | >10 µM | 8.5 µM |
| CL152 | Male | squamous cell carcinoma | Collected while chemonaive | WT | Loss | R248W | WT | intrinsic resistance | >10 µM | 12 µM |
| CL25 | Male | adenocarcinoma | Collected before erlotinib treatment, partial response | Exon 19 deletion | Normal | C135Y | WT | sensitive | 50 nM | 13 µM |
| CL97 | Male | adenocarcinoma | Collected after erlotinib and several cycles of chemotherapy, response to erlotinib use; disease progression | G719A/ T790M | Normal | R273H | WT | acquired resistance | >10 µM | 7.2 µM |
| H1975 | Female | adenocarcinoma | established in July 1988 from a non-smoker | L858R/ T790M | Normal | WT | WT | acquired resistance | >10 µM | 15 µM |
| A549 | Male | adenocarcinoma | initiated in 1972 by D.J. Giard, et al. through explant culture of lung carcinomatous tissue from a 58-year old Caucasian. | WT | Normal | WT | G12S | intrinsic resistance | >10 µM | >10 µM | tyrosine kinase inhibitor.
• The clinical information of H1975 and A549 were obtained from ATCC.
• *ND: not determined.

PHARMACEUTICAL COMPOSITION FOR TREATMENT OF CANCER USING PHENOTHIAZINE

CROSS REFERENCE TO RELATED APPLICATIONS

The present invention is a continuation of U.S. patent application Ser. No. 14/841,727 filed on Sep. 1, 2015 entitled "PHARMACEUTICAL COMPOSITION FOR TREATMENT OF CANCER USING PHENOTHIAZINE" which is, in turn, a continuation-in-part application to U.S. Ser. No. 14/354,873 National Stage Application with 371(c) date of Apr. 28, 2014 which is an US national stage patent application of PCT Application No. PCT/CN2012/083698 filed on Oct. 29, 2012, entitled "PHARMACEUTICAL COMPOSITION FOR ELIMINATION OF CANCER STEM CELLS." The present application also claims priority to provisional patent application with application No. 62/044,432 entitled "PHARMACEUTICAL COMPOSITION FOR ELIMINATION OF CANCER STEM CELLS-THIORIDAZINE AND THIORIDAZINE ENANTIOMER" filed on Sep. 2, 2014.

FIELD OF THE INVENTION

The present invention relates to a pharmaceutical composition for elimination of cancer stem cells. More specifically, the present invention relates to the use of phenothiazine for treatment of cancer.

BACKGROUND OF THE INVENTION

Development of resistance in cancer is a major issue in cancer treatments. Taking non-small cell lung carcinoma (NSCLC) as an example, seventy percent of all NSCLC patients progress to advanced stages and may need systemic therapy. Most advanced stage lung cancer patients receiving first-line chemotherapy experience disease progression[2]. Standard treatment options for NSCLC include cytotoxic combination chemotherapy (first line), such as pemetrexed (adenocarcinoma with EGFR-WT) and gemcitabine (squamous cell carcinoma) with platinum (cisplatin or carboplatin)[3-5]. Even though an initial response to these treatments is commonly observed, the overall survival with combination chemotherapy is approximately 12 months[3,4,5]. This may be due to therapy-resistant tumor cell-derived disease relapse. Therefore, the efficient killing of resistant cells is a major focus of outcome improvement.

Phenothiazines have shown promise in overcoming resistance cells. For example, thioridazine is an anti-psychotic drug that is widely used to treat schizophrenia and psychosis. It has been shown that patients with schizophrenia have a lower risk of developing cancer (1.93%) than patients without schizophrenia (2.97%)[16], and some anti-psychotic drugs have been reported to have anti-cancer effects[17,18]. Furthermore, thioridazine was reported to selectively target human somatic CSCs capable of in vivo leukemic disease initiation while having no effect on normal blood stem cells[19]. Thioridazine was also identified as a candidate anti-lung cancer stem cell agent[24]. Recent studies suggested that thioridazine has an anti-cancer effect in ovarian and cervical cancer cell lines through the phosphatidylinositol-3'-kinase (PI3K)/AKT pathway[20,21], which is a key regulator of autophagy. Thioridazine has also been reported to inhibit other human cancer cell lines, including ovarian cancer and leukemia. Thioridazine, a calmodulin antagonist, has been shown to inhibit breast cancer cell growth in vitro[22]. It is a potential adjuvant chemotherapeutic agent for the treatment of human cancer because of its cytotoxic effect on nucleic acids[23].

SUMMARY OF THE INVENTION

The present invention provides for use of racemic thioridazine, (S)-thioridazine, (R)-thioridazine or a pharmaceutically acceptable salt thereof in the manufacture of a medicament for treating cancer. In an embodiment, the invention further comprises use of one or more anti-cancer drugs in combination with the racemic thioridazine, (S)-thioridazine, (R)-thioridazine or a pharmaceutically acceptable salt thereof in the manufacture of the medicament for treating cancer. In one aspect, the anti-cancer drug is cisplatin, gefitinib, gemcitabine, pemetrexed or a combination thereof. In another aspect, the cancer comprises non-small-cell lung carcinoma (NSCLC). In yet another aspect, the cancer comprises NSCLC with KRAS mutation. In a further aspect, the cancer comprises NSCLC with KRAS wild type. In one aspect, the medicament treats cancer by inhibiting and/or eliminating cancer stem cells (CSC). In another aspect, the medicament treats cancer by activating AMPK in the CSCs. In a further aspect, the medicament treats cancer by inhibiting cholesterol synthesis enzymes in the CSCs.

The present invention further provides a pharmaceutical composition for treating a cancer comprising a therapeutically effective amount of racemic thioridazine, (S)-thioridazine, (R)-thioridazine or a pharmaceutically acceptable salt thereof. In an embodiment, the invention further comprises an anti-cancer drug. In one aspect, the anti-cancer drug is cisplatin, gefitinib, gemcitabine, pemetrexed or a combination thereof. In another aspect, the racemic thioridazine, (S)-thioridazine, (R)-thioridazine or a pharmaceutically acceptable salt thereof in combination with the anti-cancer drug are in the form of one formulation or multiple formulations. In a further aspect, the effective amount of racemic thioridazine, (S)-thioridazine, (R)-thioridazine or a pharmaceutically acceptable salt thereof treats cancer by inhibiting and/or eliminating CSCs. In an aspect, the cancer is NSCLC. In another aspect, the cancer is NSCLC with KRAS mutation. In a further aspect, the cancer is NSCLC with KRAS wild type. In a further aspect, the racemic thioridazine, (S)-thioridazine, (R)-thioridazine or a pharmaceutically acceptable salt thereof treats cancer by activating AMPK in CSCs. In one aspect, the racemic thioridazine, (S)-thioridazine, (R)-thioridazine or a pharmaceutically acceptable salt thereof treats cancer by inhibiting cholesterol synthesis enzymes in CSCs.

The present invention also provides a method for treating cancer in a subject, comprising administering to the subject in need a therapeutically effective amount of a pharmaceutical composition comprising racemic thioridazine, (S)-thioridazine, (R)-thioridazine or a pharmaceutically acceptable salt thereof, and a pharmaceutically acceptable carrier. In an embodiment, the method further comprises the administration of an anti-cancer drug. In one aspect, the anti-cancer drug comprises cisplatin, gefitinib, gemcitabine, pemetrexed or a combination thereof. In another aspect, the cancer comprises lung cancer. In a further aspect, the lung cancer comprises non-small cell lung cancer. In one aspect, the lung cancer comprises NSCLC with KRAS mutation. In a further aspect, the cancer comprises lung cancer. In a further aspect, the lung cancer comprises non-small cell lung cancer. In one aspect, the lung cancer comprises NSCLC with KRAS wildtype. In yet another aspect, the lung cancer is resistant to gefitinib, erlotinib, cetuximab, matuzumab, or panitumumab.

The present invention further provides a method for selecting clinical trial subjects for racemic thoridazine, (S)-thioridazine, (R)-thioridazine or a pharmaceutically acceptable salt thereof for treating NSCLC comprising the step of selecting clinical trial subjects who are afflicted with NSCLC with KRAS mutation.

BRIEF DESCRIPTION OF THE DRAWINGS

The foregoing summary, as well as the following detailed description of the invention, will be better understood when read in conjunction with the appended drawing. In the drawings:

FIG. 1B provides the results of CL141 cell line that was incubated with DMSO or the indicated concentrations of trifluoperazine for 48 hrs, in which the numbers indicate the percentages of total cells in the corresponding quadrant; the bottom right quadrant is the early apoptotic cells, and the top right quadrant is late apoptotic cells; FIG. 1C shows the results of side population assay, in which the cancer stem-like side population was significantly decreased by trifluoperazine (5 µM), from 2.13% to 0.11% in CL141 cells, and from 1.95% to 0.06% in CL152 cells; FIG. 1D shows that the aldehyde dehydrogenase (ALDH)-positive subpopulation of cancer stem-like cells was reduced by trifluoperazine (5 µM), from 4.31% to 0.84% in CL141 cells, and from 3.73% to 1.08% in CL152 cells; and FIG. 1E shows that trifluoperazine dose-dependently activated apoptotic signaling in CL97 spheroids, including Bax, Bak, and cleaved PARP, caspase-3, and caspase-9, whereas the anti-apoptotic proteins Bcl-2, XIAP, and Mcl-1 were down-regulated. All values are the average of triplicate experiments with the S.D. indicated by the error bars, and there are statistically significant differences, for example, between treatment with and without trifluoperazine (* $P<0.05$, ** $P<0.01$).

FIG. 2C provides the images of CL141 colonies taken under phase microscopy (top panel) and the number of the colonies (bottom panel) calculated after two weeks of treatment with trifluoperazine, in which colonies containing >50 cells were counted and the number of colonies in the control group was set at 100% (N=3,  $P<0.01$); FIG. 2D provides the expression of CD44 and CD133 in CL141 and CL97 cancer spheroids after being treated with different doses of trifluoperazine for 48 hrs, in which the expression was evaluated by Western blot analysis, and β-actin served as an internal control; FIG. 2E provides immunostained images for CD133 and nuclei counterstaining (DAPI) of various spheroids at 48 hrs after trifluoperazine (TFP) treatment, in which photomicrographs were taken at 40× magnification; FIG. 2F provides the expression of c-Myc, cyclin D1 and c-Met in CL97 cancer spheroids after being treated with different doses of trifluoperazine for 48 hrs, in which the expression was evaluated by Western blot analysis, and β-actin served as an internal control; and FIG. 2G provides TCF/LEF transcription following treatment of CL141 cancer spheroids with different concentrations of trifluoperazine for 24 hrs, in which cells were lysed before the TOPflash and FOPflash activities were recorded in a luminometer (N=3, * $P<0.05$, ** $P<0.01$).

FIGS. 3A-H provide trifluoperazine effects in combination therapy with cisplatin or gefitinib, wherein FIG. 3A shows the half maximal inhibitory concentration of the conventional chemotherapy drug cisplatin on various NSCLC spheroids (SP) and their corresponding parental cells; FIGS. 3B and 3C show the results of cell viability assay and caspase-3 activity assays, respectively, for various NSCLC spheroids treated with cisplatin (10 µM) for 24 hrs; FIG. 3D shows the results of cell number measurements of CL83 and CL141 cancer spheroids after treatment with trifluoperazine in combination with cisplatin; FIG. 3E provides assessment of the combination of trifluoperazine and gefitinib by isobologram analysis, in which normalized isobolograms for EGFR-wide type (CL141) and EGFR mutation cells (CL97 and CL25) exposed to all possible drug combinations of trifluoperazine (0.5, 2.5 and 5 µM) and gefitinib (2.5, 5 and 10 µM) for 48 hrs are shown; symbols designate the combination index value for each fraction affected; the curves were generated by Calcusyn software to fit the experimental points; the data are representative of 3 independent experiments; values below the line are synergistic, whereas those close to the line are additive and those above the line antagonistic; FIG. 3F shows the results of cell number measurements of CL141, CL97, and CL25 spheroids treated with trifluoperazine (10 µM), gefitinib (5 µM), or both (TFP+Gef), respectively, for 48 hrs; FIG. 3G provides the percentages of ALDH$^+$ cells in CL141 cells, which was analyzed by flow cytometry; and FIG. 3H shows that trifluoperazine enhanced gefitinib inhibition of CL141 self-renewal; disaggregated CL141 spheroids were seeded at clonal density on low adhesion plates for secondary cancer spheroid formation. All values are the average of triplicate experiments with the S.D. indicated by the error bars (** $P<0.01$).

FIGS. 4A-C provide in vivo monitoring of trifluoperazine-mediated anti-tumor effects; wherein FIG. 4A shows representative bioluminescent images of CL97-bearing mice over the period of 4 weeks (top panel) and changes in bioluminescence intensity (BLI) were measured and plotted as fold change in BLI over time (bottom panel), in which CL97 bulk tumor cells were intravenously injected into NOD/SCID mice that subsequently received different treatments, namely vehicle (control), trifluoperazine (TFP) (5 mg/kg/day), gefitinib (150 mg/kg/day, oral gavage), and combination of gefitinib (100 mg/kg/day, oral gavage) and trifluoperazine (5 mg/kg/day, i.p); the tumor burden was measured and judged by the fold changes in bioluminescence, and ranked in decreasing order as follows: vehicle control >gefitinib >trifluoperazine >combined treatment; notably, tumor burden between mice receiving vehicle and gefitinib was not significantly different, and the tumor burden in mice which received the combined treatment was significantly lower than that of mice receiving trifluoperazine treatment (* $P<0.05$) and those receiving vehicle or gefitinib (** $P<0.01$); FIG. 4B shows representative bioluminescent images (top panel) of NOD/SCID mice, in which vehicle- and trifluoperazine-pretreated (5 µM<IC50, overnight treatment) CL97 tumor spheroids were orthotopically injected into the lung of the NOD/SCID mice for tumorigenic ability tests; in-situ tumor growth was significantly delayed and suppressed in trifluoperazine-pretreated animals (top panel), where the measurement of the tumor burden plotted as fold change in BLI (bottom panel) shows significant difference between the two groups (* P<0.05); and FIG. 4C demonstrates that samples from the combined treatment of trifluoperazine and gefitinib (Comb) provided the most significant suppression of β-catenin, c-Myc and cyclin D1 expression as compared to those from the treatment of trifluoperazine alone, gefitinib alone and vehicle control, whereas the expression level of caspase-3, a pro-apoptotic molecule, was increased in all treatment groups except for the vehicle control; similarly, β-catenin, c-Myc and cyclin D1 expression levels were suppressed in trifluoperazine-pretreated tumor spheroids while activated caspase-3 expression was increased. Total cell lysates were harvested from tumor biopsies of mice which received different treatments and their protein profiles were examined.

FIG. 5A shows the ability of thioridazine in inhibiting the capacity of lung cancer spheroid self-renewal. Treatment with thioridazine for 48 hrs resulted in decreases in the number of CL141 and CL97 spheroids. FIG. 5B shows that the cancer stem-like side population was reduced by thioridazine treatment. In FIG. 5C, the aldehyde dehydrogenase (ALDH) activity was analyzed by flow cytometry. As shown in FIG. 5C, the percentages of ALDH$^+$ cells were significantly reduced by the treatment with thioridazine.

FIGS. 6A and 6B respectively illustrate results of A549 and CL141 spheres that were treated with 5 µM thioridazine for 24 hrs, and were subsequently subjected to ALDH activity determination. DEAB was used to establish the baseline fluorescence of these cells and to define the ALDEFLUOR-positive region. The DEAB (−) referred to as cells were treated with DMSO and served as a negative control, whereas the DEAB (+) was used as a positive control. (S)-thioridazine exhibited the most pronounced effect than (R)-thioridazine or unpurified thioridazine (referred to as racemic thioridazine and will use thioridazine in this study) on the ALDH activity inhibition in these cells. FIGS. 6C and 6D illustrate the result of sphere formation assay of A549 and CL141 spheres, respectively, when treated with 5 µM thioridazine for 24 hrs. As shown in FIGS. 6C and 6D, the (S)-thioridazine had the most effective impact on the sphere viability inhibition. * P<0.05,  P<0.01, * P<0.01, N=3.

FIG. 7A shows inhibition of HMG-CoA reductase activity by (R)-thioridazine treatment, FIG. 7B shows inhibition of HMG-CoA reductase activity by (S)-thioridazine treatment and FIG. 7C shows inhibition of HMG-CoA reductase activity by thioridazine treatment. The recombinant HMG-CoA reductase was coadministered with (S)-thioridazine, (R)-thioridazine and thioridazine, at 0.01, 0.1, 1, and 5 µM in vitro, respectively, and the activity was further measured as indicated by the absorbance of NADPH. Comparing, FIGS. 7A-C, (S)-thioridazine more effectively inhibited the activity of HMG-CoA reductase than thioridazine and (R)-thioaridazine. FIG. 7D illustrates the activity of HMG-CoA reductase with (S)-thioridazine, (R)-thioridazine and thioridazine treatments where * P<0.05,  P<0.01, * P<0.001 versus DMSO control, N=3.

FIG. 8A shows results for A549 cells and FIG. 8B shows results for CL141 cells. A549 and CL141 cells were treated with thioridazine at 0.01, 0.1 and 1 µM for 24 hrs. Cell lysates were then subjected to Western blot analysis to investigate the AMPK and cholesterol biosynthesis pathways. * P<0.05,  P<0.01, * P<0.001 versus DMSO control, N=3. The mevalonate-related pathway was regulated via AMPK signaling, including the HMGCR, FDFT1, and IDI1. Consequently, the expression of these proteins was also compared between the A549 (mutant cells) and CL141 (KRAS wild-type) after the treatment with thioridazine. The data suggested that the downstream of AMPK signaling was affected more obviously via (S)-thioridazine than (R)-thioridazine treatment in A549 cell.

FIG. 9A shows results for A549 sphere and FIG. 9B shows results for CL141 spheres. After treatment with thioridazine for 24 hrs, the expression of the stemness markers and cholesterol-biosynthesis enzymes from A549 spheres and CL141 cells was further determined via Western blot. As shown in the figures, (S)-thioridazine had a more obvious impact than (R)-thioridazine and thioridazine on the stemness markers and the cholesterol biosynthesis enzymes inhibition.

FIG. 10A illustrates identification of the potential biomarker for thioridazine treatment via the Catalogue of Somatic Mutations In Cancer (COSMIC) analysis. The scatter plot shows the experimental data about $Log_e$ (IC50) of AICAR in NSCLC cell lines (y axis) versus KRAS gene type from these NSCLC cell lines (x axis). The $Log_e$ (IC50) of the cell lines with wild-type and mutated KRAS are labeled with dots, respectively. Each dot of the scatter plot represents each NSCLC cell line. AICAR is significantly more sensitive to the NSCLC cells with KRAS mutation than KRAS wild-type cells (one-sided t test, * P<0.05). However, other mutations frequently observed in NSCLC cells show no significant difference in IC50 toward AICAR. FIG. 10B illustrates that colony formation ability of the KRAS wild-type and the mutant cell lines was reduced after exposure to thioridazine and its enantiomers at 5 µM, respectively. As shown in FIG. 10B, (S)-thioridazine was more effective than (R)-thioridazine at colony inhibition in the KRAS mutant cell lines (A549, H460 and H441). FIG. 10C illustrates the statistical significance of the colony formation results was summarized, N=3.

FIG. 11A shows results for CL141 cells treated with (R)-thioridazine, FIG. 11B shows results for CL141 cells treated with (S)-thioridazine, FIG. 11C shows results for CL152 cells treated with (R)-thioridazine and FIG. 11D shows results for CL152 cells treated with (S)-thioridazine. As shown in the FIGS. 11A-D, both CL141 and CL152 cells were more sensitized to (S)-thioridazine than (R)-thioridazine after $KRAS^{G12D}$ transfection. ** P<0.01, N=3.

FIG. 12A illustrates transfection efficiency as evaluated by Western blot. FIG. 12B illustrate results of IC50 calculations that compare effects of each enantiomer. After the dominant negative AMPK transfection, A549 cells were further treated with (S)-thioridazine and (R)-thioridazine from 0.1 μM to 5 μM for 48 hrs, and the cell viability was determined via SRB assay as shown in FIGS. 12C and 12D. As seen in FIGS. 12C and 12D, cell viability was inhibited by (S)-thioridazine through AMPK activation, while cell viability inhibition via (R)-thioridazine was not dependent upon AMPK activation. ** $P<0.01$, N=3.

FIGS. 15A-E illustrate effectiveness of thioridazine, its enantiomers and trifluoperazine either alone or in combination with pemetrexed in inhibiting H441 tumor growth. FIG. 15A are representative bioluminescence images of H441 NSCLC-bearing mice under the four drug treatments. The treatments were initiated approximately one week post tumor injection, ensuring an approximately even bioluminescent intensity in all mice. The bioluminescence intensity was collected weekly for the purpose of monitoring tumor burden. FIG. 15B summarizes comparative bioluminescence analysis of the four treatment groups in vivo at 5 mg/kg dosage. As can be seen in FIG. 15B, based on the fold change in bioluminescence intensity, thioridazine and its enantiomers (5 mg/kg) as well as trifluoperazine (5 mg/kg) significantly suppressed the tumorigenesis of H441 as compared with the vehicle-treated control animals. Note that the standard errors of fold-change relative to the control group appear quite large due to the rapid tumor growth in the vehicle-treated group from week 3 on. FIG. 15C summarizes comparative tumor-inhibitory effect mediated by thioridazine in vivo at 3 mg/kg dosage. Tumor suppressive effect of 3 different forms of thioridazine (3 mg/kg) was examined in H441-bearing mice over a period of 5 weeks. The change in tumor burden was quantified as the fold change in tumor size (measured by caliper) over time. (S)-thioridazine-treated mice exhibited the most significant tumor inhibitory effect compared with (R)-thioridazine and thioridazine (tumor sizes were not significantly different at week 5). FIG. 15D summarizes comparative tumor-inhibitory effect mediated by pemetrexed, pemetrexed+(S)-thioridazine, pemetrexed+(R)-thioridazine and pemetrexed+thioridazine (racemate) at 1 mg/kg. Specifically, combination treatment with pemetrexed, thioridazine and (R)-thioridazine (at 1 mg/kg) showed similar tumor suppressive effects as compared to the pemetrexed alone group. However, (S)-thioridazine (1 mg/kg) and pemetrexed combined treatment appeared to suppress the tumor growth to the greatest extent among all treatment groups. In FIG. 15E, tumor biopsies were collected from the (S)-thioridazine, (R)-thioridazine and thioridazine treatment groups, respectively, and further subjected to Western blot analysis. The results of the analysis are shown in FIG. 15E. In FIG. 15C, * $P<0.05$ thioridazine treatment versus DMSO.  $P<0.01$ (S)-thioridazine and (R)-thioridazine treatment versus DMSO.

FIG. 18 summarizes the results from the MTT, side population, and clonogenic assays. Six of the antipsychotics tested, including trifluoperazine, thioridazine, chlorpromazine, perphenazine, triflupromazine and promazine, were found to reduce the percentages (>50%) of side population cells among CL141 cells.

FIG. 19 The clinical characteristics, gene mutations, and responses to EGFR-TKI and trifluoperazine for the non-small cell lung cancer cell lines in this study.

DESCRIPTION OF THE INVENTION

Figure 1:
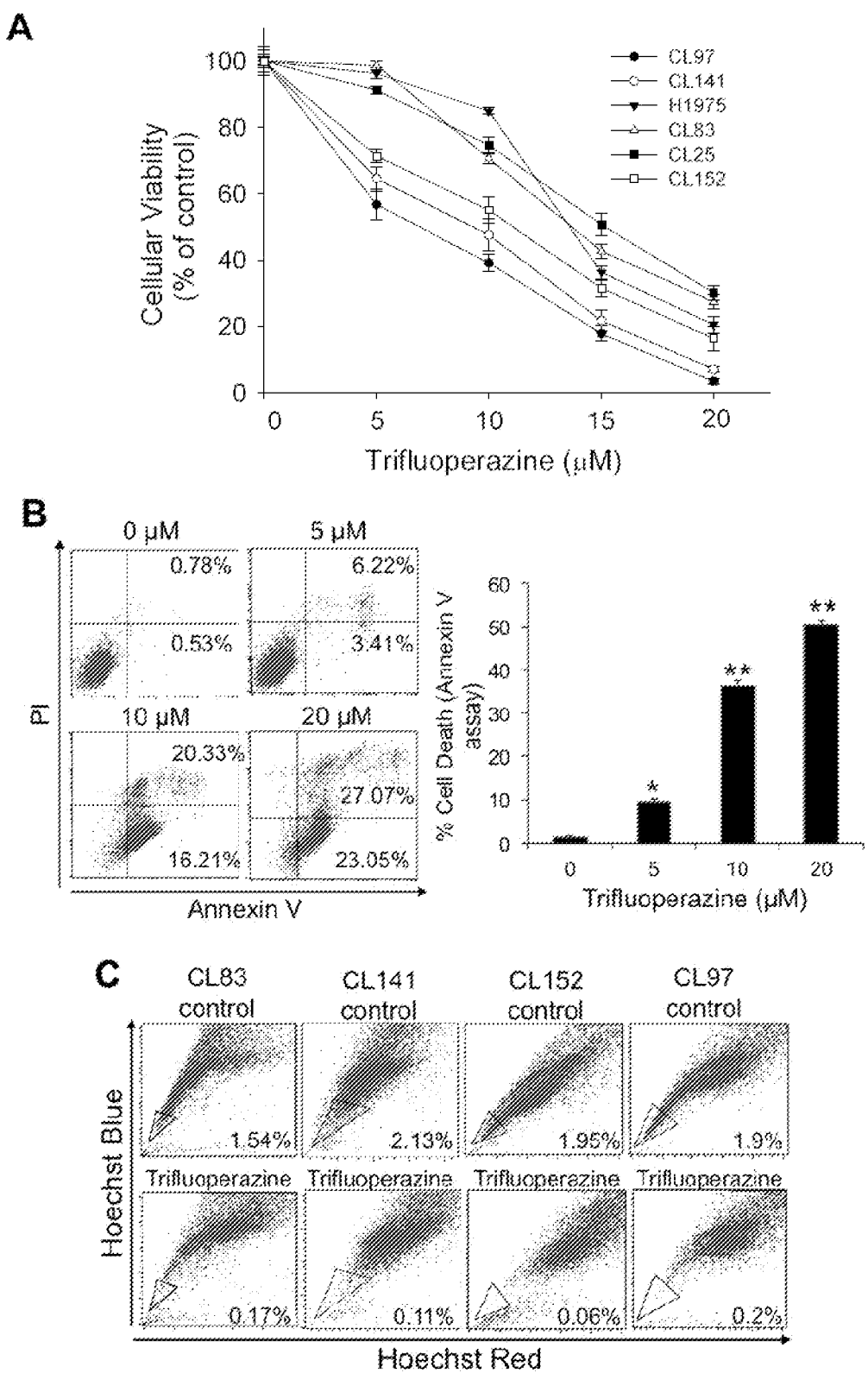
FIGS. 1A-E provide the effects of trifluoperazine in inhibiting proliferation and inducing apoptosis of gefitinib-resistant NSCLC cells, wherein FIG. 1A provides the results of various NSCLC cells in 96-well plates that were treated with trifluoperazine for 48 hrs, in which cell viability was measured by the MTT assay.
Figure 1:
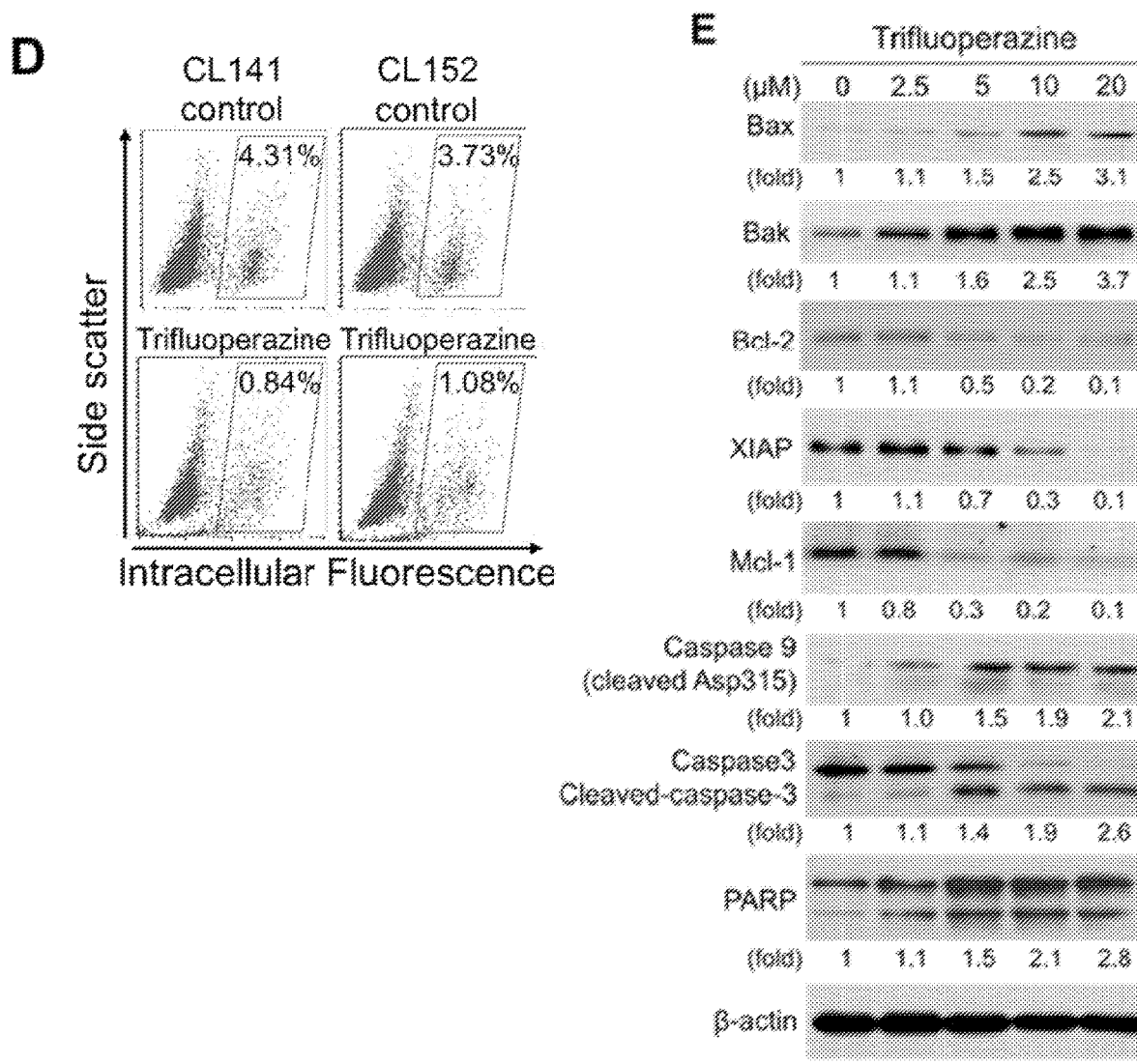

Unless defined otherwise, all technical and scientific terms used herein have the same meaning as commonly understood by a person skilled in the art to which this invention belongs.

As used herein, the singular forms "a", "an" and "the" include plural referents unless the context clearly dictates otherwise. Thus, for example, reference to "a sample"

includes a plurality of such samples and equivalents thereof known to those skilled in the art.

The phrase "eliminating cancer stem cells" as used herein refers to a process of reducing the number of and/or inhibiting clonogenicity and stemness-associated markers of CSCs to an extent that the tumor initiating ability thereof can be suppressed.

The phrase "anti-CSC property" as used herein refers to property of eliminating cancer stem cells as well as any other ways of eliminating or inhibiting growth of CSC as known in the art.

As used herein, the term "anti-cancer drug" refers to any drug providing anti-cancer effect, including but not limited to gefitinib, cisplatin, Tarceva, pemetrexed, and anti-EGFR antibody. In embodiments of the invention, the anti-cancer drug is preferably gefitinib, pemetrexed or cisplatin.

The term "thioridazine" without (S)- or (R)-prefix as used herein refers to racemic form of thioridazine.

As used herein, the term "antipsychotic phenothiazine derivatives", "antipsychotic" or "anti-psychotic drug" refers to a group of compounds having the structure of formula I:

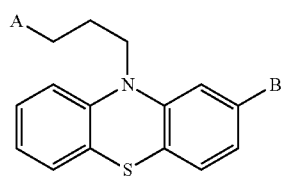

Formula I wherein the 10H-phenothiazine derivatives bear an alkyl substituent, in which A is $N(CH_3)_2$, a N-methyl or N-ethyl piperazinyl group, a N-(hydroxyethyl)piperazinyl group, or a N-methyl piperidinyl group, and B is $SCH_3$, Cl, $CF_3$, or H.

According to the invention, examples of the compound having the structure of formula I include but are not limited to the anti-psychotic drugs as shown below.

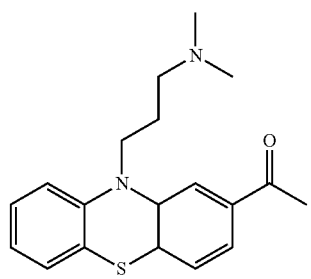

Acepromazine

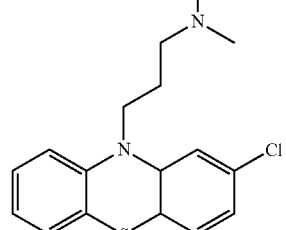

Chloropromazine

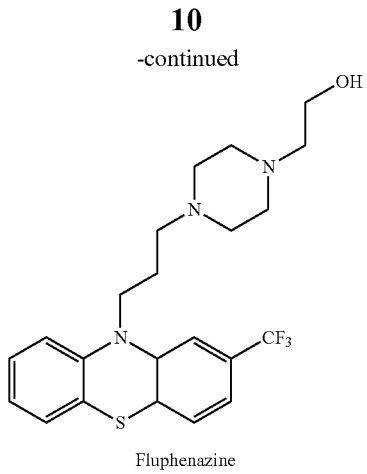

Fluphenazine

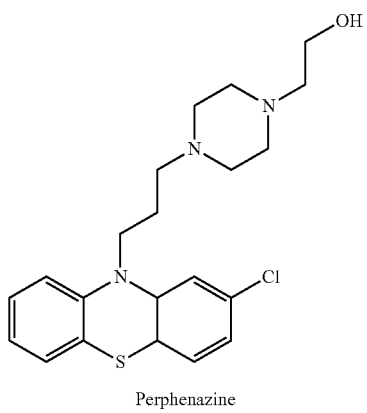

Perphenazine

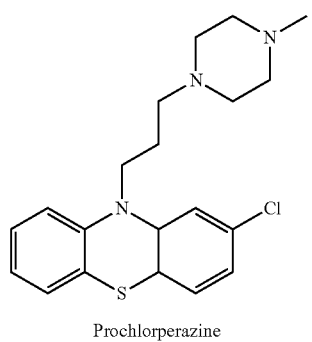

Prochlorperazine

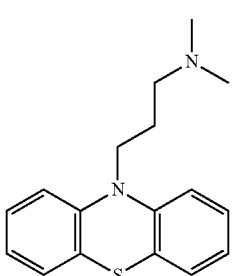

Promazine

Thioridazine

Trifluoperazine

Triflupromazine

Promethazine

According to the invention, it was unexpectedly found that some of known antipsychotic phenothiazine derivatives have anti-CSC effects.

In this invention, CSC-like cells isolated from the CL141 cell line using side population technique were enrolled to examine the potential anti-CSC effects of some of the known antipsychotics. FIG. 18 summarizes the results from the MTT, side population, and clonogenic assays. Six of the antipsychotics tested, including trifluoperazine, thioridazine, chlorpromazine, perphenazine, triflupromazine and promazine, were found to reduce the percentages (>50%) of side population cells among CL141 cells (FIG. 18).

Therefore, according to the invention, the anti-psychotic drug as a cancer stem cell inhibitor may be trifluoperazine, thioridazine, chlorpromazine, perphenazine, triflupromazine and promazine.

Further in vitro and in vivo experiments demonstrated that such compounds, particularly trifluoperazine, thioridazine and thioridazine enantiomers, are capable of eliminating cancer stem cells, such as lung CSCs (see Examples).

Accordingly, the invention provides use of a compound having the structure of formula I in the manufacture of a medicament for eliminating cancer stem cells (CSCs):

Formula I wherein A is $N(CH_3)_2$, a N-methyl or N-ethyl piperazinyl group, a N-(hydroxyethyl)piperazinyl group, or a N-methyl piperidinyl group, and B is $SCH_3$, Cl, $CF_3$, or H. For example, the compound having the structure of formula I may be trifluoperazine, chlorpromazine, thioridazine, thioridazine enantiomers, perphenazine, triflupromazine, promazine or a combination thereof.

Figure 4:
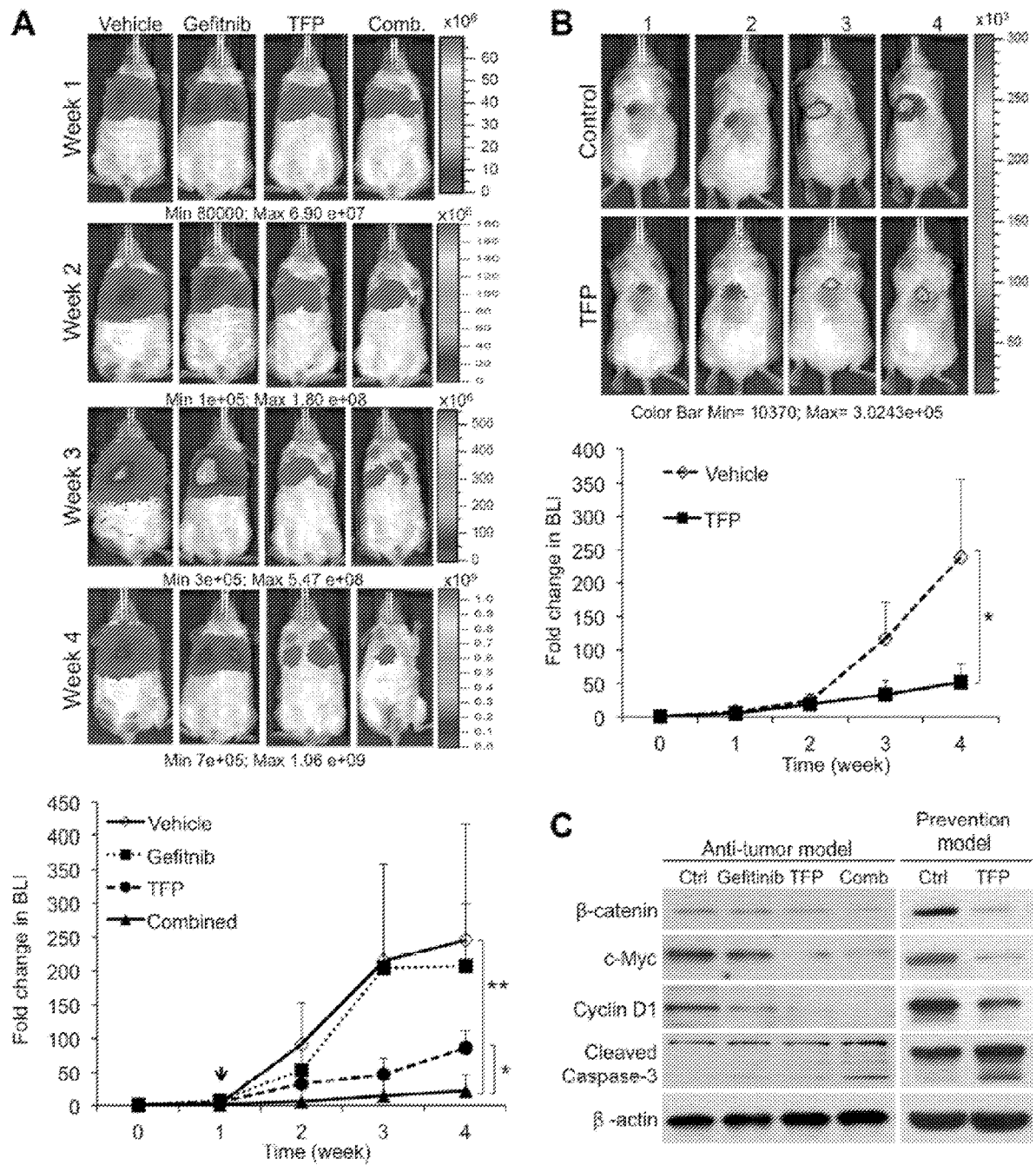

In one embodiment of the invention, the compound having structure of formula I is trifluoperazine, which has the structure of Unexpectedly, it was also found that trifluoperazine alone significantly reduced in-situ tumor growth as compared to vehicle-treated control in a prevention experiment, in which CL97-L2G cells were pre-treated with trifluoperazine before orthotopically implanted into NOD/SCID mice (FIG. 4B).

Thus, the present invention also provides use of formula I as above mentioned in the manufacture of a medicament for preventing a cancer.

In addition, it was also confirmed in the invention that trifluoperazine in combination with an anti-cancer drug provides a synergistic effect in inhibiting the growth of CSCs, and in reducing drug resistance. In one embodiment of the invention, the compound of formula I at an effective amount can be administered in combination with an anti-cancer drug to provide a synergistic effect in eliminating cancer stem cells and in reducing drug resistance of a cancer.

It is further demonstrated in the invention that trifluoperazine treatment suppressed tumorigenesis of gefitinib-resistant tumor cells in the lung cancer animal model (see Examples).

Accordingly, further provided in the invention is a method for treating a cancer in a subject resistant to standard chemotherapeutic treatments comprising administering to the subject a therapeutically effective amount of trifluoperazine in combination with an anti-cancer drug, wherein the anti-cancer drug is administered to the subject before, simultaneously with or after the administration of trifluoperazine. In embodiments of the invention, the method can reduce the resistance to the standard chemotherapeutic treatments and inhibit the growth of CSCs.

According to the invention, the anti-cancer drug and the trifluoperazine to be administered simultaneously may be formulated into two separate pharmaceutical compositions or one pharmaceutical composition.

As used herein, the term "effective amount" or "therapeutically effective amount" refers to an amount sufficient for eliminating cancer stem cells or reducing drug resistance of a cancer, which is depending on the mode of administration and the condition to be treated, including age, body weight, symptom, therapeutic effect, administration route and treatment time. For example, the effective amount of trifluoperazine may be 10 to 60 mg/day, preferably 20 to 50 mg/day, or more preferably 35-45 mg/day.

For a patient with early-stage lung cancer, e.g., non-small cell lung cancer (NSCLC), a surgical resection remains the mainstay treatment; however, the reported failure rate in stage I NSCLC ranges from 27% to 38%, and about 90% cancer deaths are associated with tumor recurrence or metastasis. In this invention, it was demonstrated that at 3 or 4 weeks after treatment in a NOD/SCID mice model bearing CL97 bulk tumor cells, both trifluoperazine alone or a combination of trifluoperazine and gefitinib significantly reduced tumor burden in mice, whereas the treatment of gefitinib alone resulted in no effects in suppressing tumor recurrence (FIG. 4A).

Therefore, also provided in the present invention is a pharmaceutical composition for preventing or delaying cancer recurrence comprising a therapeutically effective amount of trifluoperazine and an anti-cancer drug, such as gefitinib or cisplatin.

In another embodiment of the invention, the compound having structure of formula I is thioridazine. Thioridazine is a stereoisomer whose enantiomers have structures below:

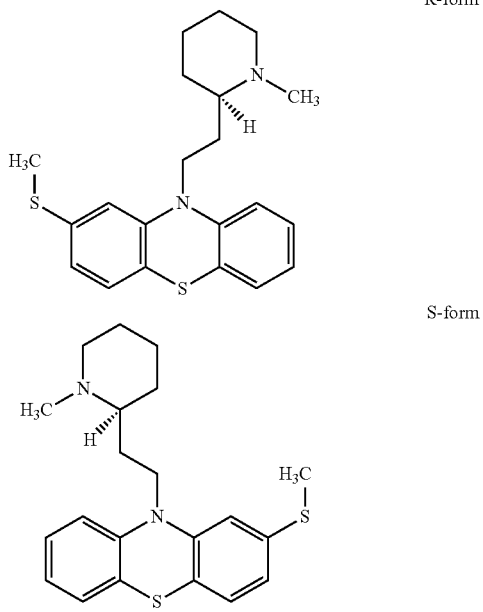

Unexpectedly, it was found that thioridazine significantly inhibits self-renewal of CL141 and CL97 cancer spheres as well as reduced side population cells and ALDH$^+$ cells in CL141 and CL97 cell lines, indicating that thioridazine alone is effective in inhibiting the growth of and elimination of CSCs and in reducing drug resistance. (See FIGS. 5A-C, 6A-D, 9A-B and 14A-C as well as Examples).

Accordingly, one embodiment of the present invention provides for use of thioridazine in the manufacture of a medicament for treating cancer. Additionally, another embodiment of the invention provides a method for treating cancer comprising administering to the subject a therapeutically effective amount of thioridazine. Furthermore, in yet another embodiment of the present invention provides for a pharmaceutical composition for treating cancer comprising thioridazine.

Figure 15:
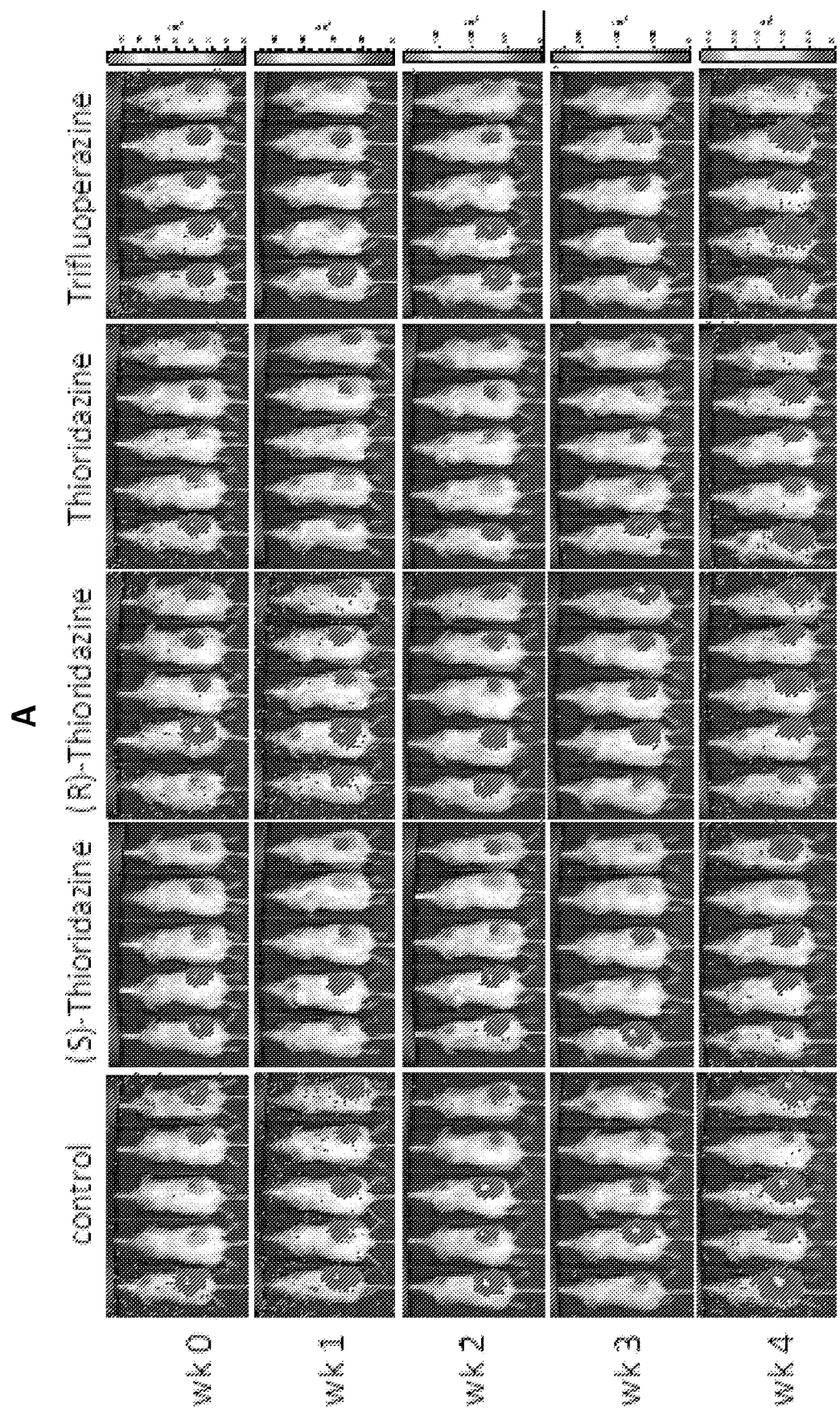
In FIG. 15**D, * $P<0.05$ (R)-thioridazine and thioridazine combined pemetrexed treatment versus DMSO. ** $P<0.01$ (S)-thioridazine combined pemetrexed treatment versus DMSO.
Figure 15:
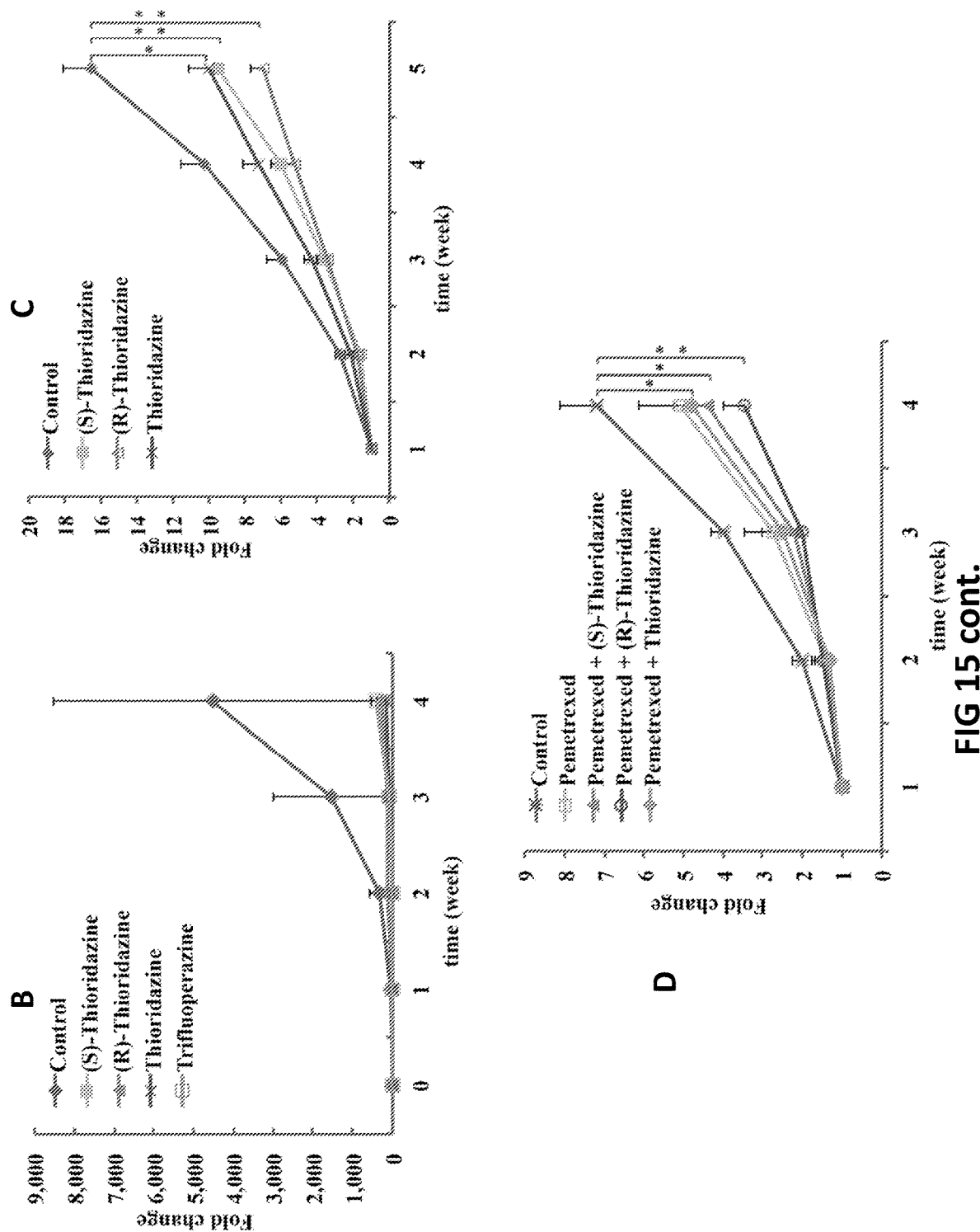
Figure 15:
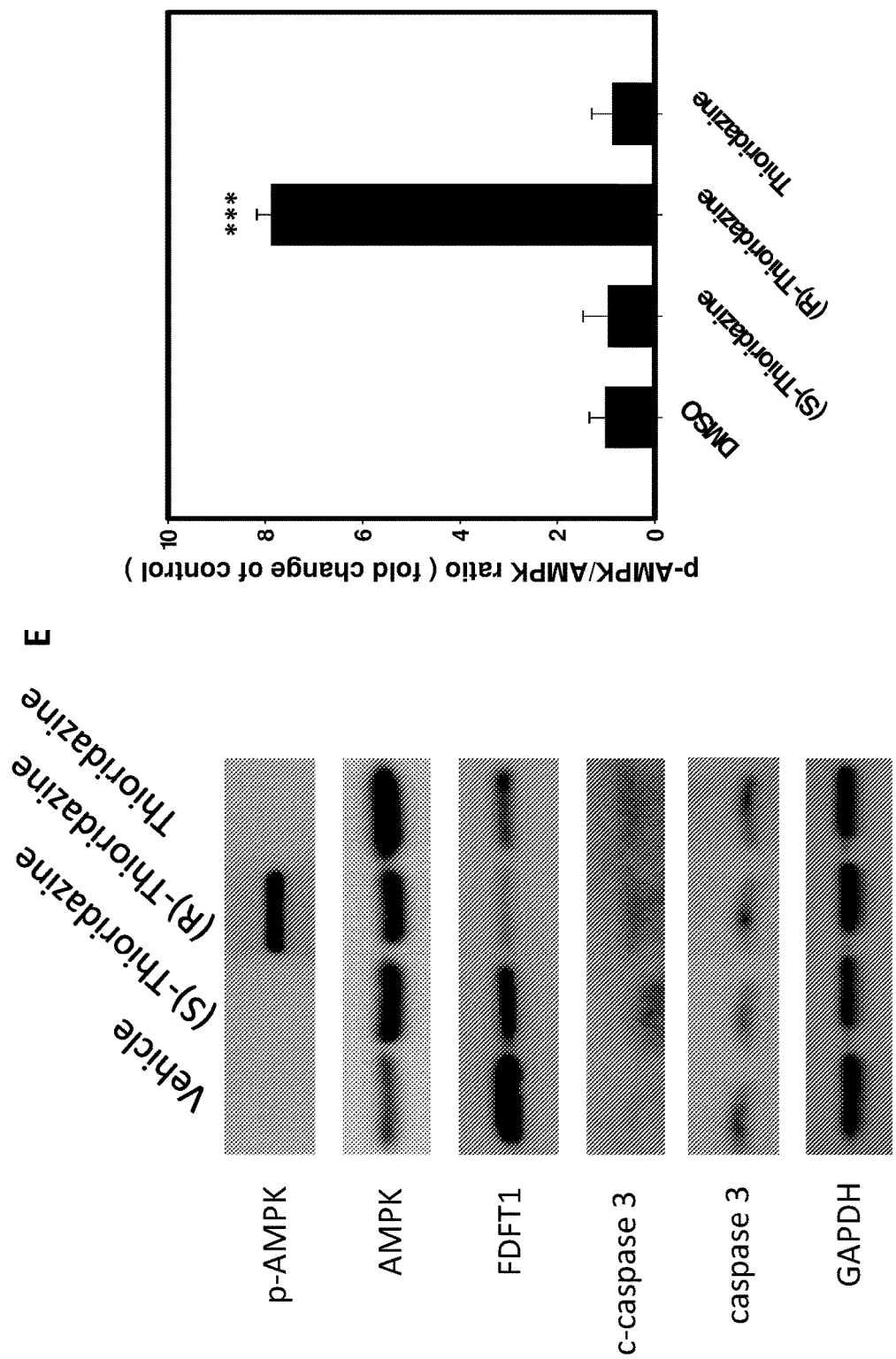
Figures 16, 17:
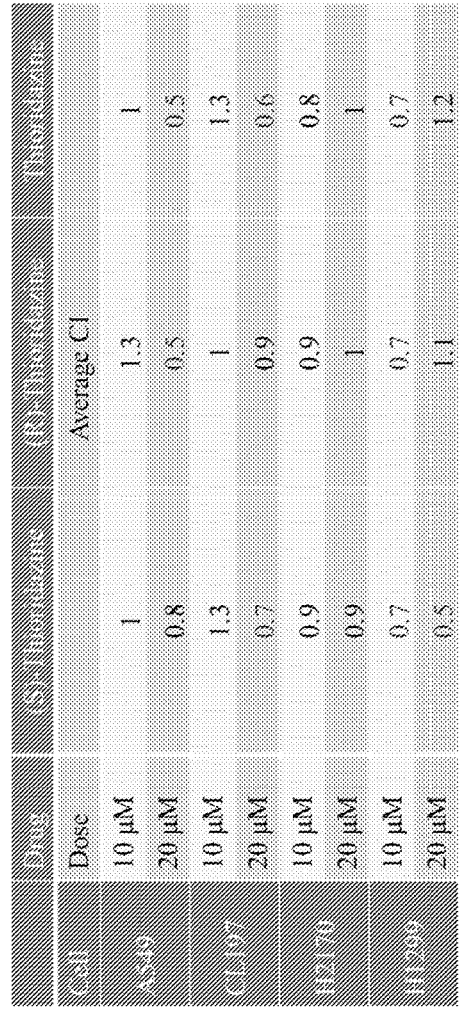
FIG. 16 illustrates incidences of catalepsy in rats caused by (S)-thioridazine, (R)-thioridazine and unpurified thioridazine treatment with control NaCl. Catalepsy was evaluated by placing rat's forepaws on a rod suspended 10 cm above bench level at 30 minutes post-dosing and scored positive if this abnormal posture is maintained for more than 5 seconds. Activity is considered significant when positive score was observed in 50 percent or more (>50) of the animals.
FIG. 17 illustrates synergy between thioridazine and gemcitabine in the elimination of NSCLC cells. Cells were exposed to thioridazine and its enantiomers and gemcitabine simultaneously for 48 hrs as indicated. The average CI values were calculated from each individual dose (10 or 20 μM) of thioridazine and its enantiomers. The values of the CIs are: CI>1, antagonism; CI=1, additivity; CI<1, synergism. The lowest CI value indicates the best synergistic effect of the combination of two drugs for inhibition of cell viability.

Further studies show that thioridazine in combination with an anti-cancer drug synergistically enhances cytotoxicity in vitro and inhibits tumors in vivo. Specifically thioridazine had a synergistic effect in combination with cisplatin in CL152 cells (FIGS. 13A-B) and thioridazine combined with gemcitabine showed similar synergistic effects in A549, H2170, H1299 and CL97 cell lines (FIG. 17). In addition, thioridazine (FIG. 15A-C) and thioridazine combined with pemetrexed (FIG. 15D) demonstrated tumor suppressive effects in H441-bearing mice. (FIGS. 13A-B, 15A and D and FIG. 17 as well as Examples).

Accordingly, further provided in the invention is use of thioridazine and an anti-cancer drug in the manufacture of a medicament for treating cancer. The medicament can be formulated in one formulation or multiple formulations. In another embodiment of the present invention provides for a method for treating cancer comprising administering to the subject a therapeutically effective amount of thioridazine in combination with an anti-cancer drug, wherein the anti-cancer drug is administered to the subject before, simultaneously with or after the administration of thioridazine.

According to an embodiment of the invention, the anti-cancer drug and thioridazine to be administered simultaneously may be formulated into two separate formulations or one single formulation.

As used herein, the term "effective amount" or "therapeutically effective amount" refers to an amount sufficient for eliminating cancer stem cells or reducing drug resistance of a cancer that is dependent on the mode of administration and the condition to be treated, including age, body weight, symptom, therapeutic effect, administration route and treatment time. For example, the effective amount of thioridazine may be 10 to 800 mg/day, preferably 20 to 50 mg/day, or more preferably 20-30 mg/day.

Furthermore, an embodiment of the present invention provides for a pharmaceutical composition comprising thioridazine and an anti-cancer drug for treatment of cancer wherein the pharmaceutical composition can comprise one formulation or two separate formulations.

Having unexpectedly found that thioridazine has anti-cancer properties, further studies were conducted to establish anti-cancer properties of thioridazine enantiomers. Accordingly, CSC-like cells isolated from A549 and CL141 cancer cells were enrolled to examine the potential effects of (S)- and (R)-thioridazine and racemic thioridazine on cancer stem cells. It was unexpected found that (S)- and (R)-thioridazine each possesses anti-CSC properties in vitro and in vivo. Specifically, (S)- and (R)-thioridazine each demonstrated suppressive effect on NSCLC cancer cell self-renewal, as well as reduces the numbers of ALDH$^+$ cells and side population cells in A549 and CL141 cells. Furthermore, it was unexpected found that (S)-thioridazine is more effective than (R)- or racemic thioridazine in inhibiting CSC. (See FIGS. 6A-D and 9A-B as well as Examples) Accordingly, one embodiment of the present invention provides use of (S)- or (R)-thioridazine in the manufacture of a medicament for treating cancer. Additionally, an embodiment of the present invention provides a method for treating cancer comprising administration to a subject a therapeutically effective amount of (S)- or (R)-thioridazine. Furthermore, yet another embodiment of the present invention provides for a pharmaceutical composition for treating cancer comprising (S)- or (R)-thioridazine.

Figure 12:
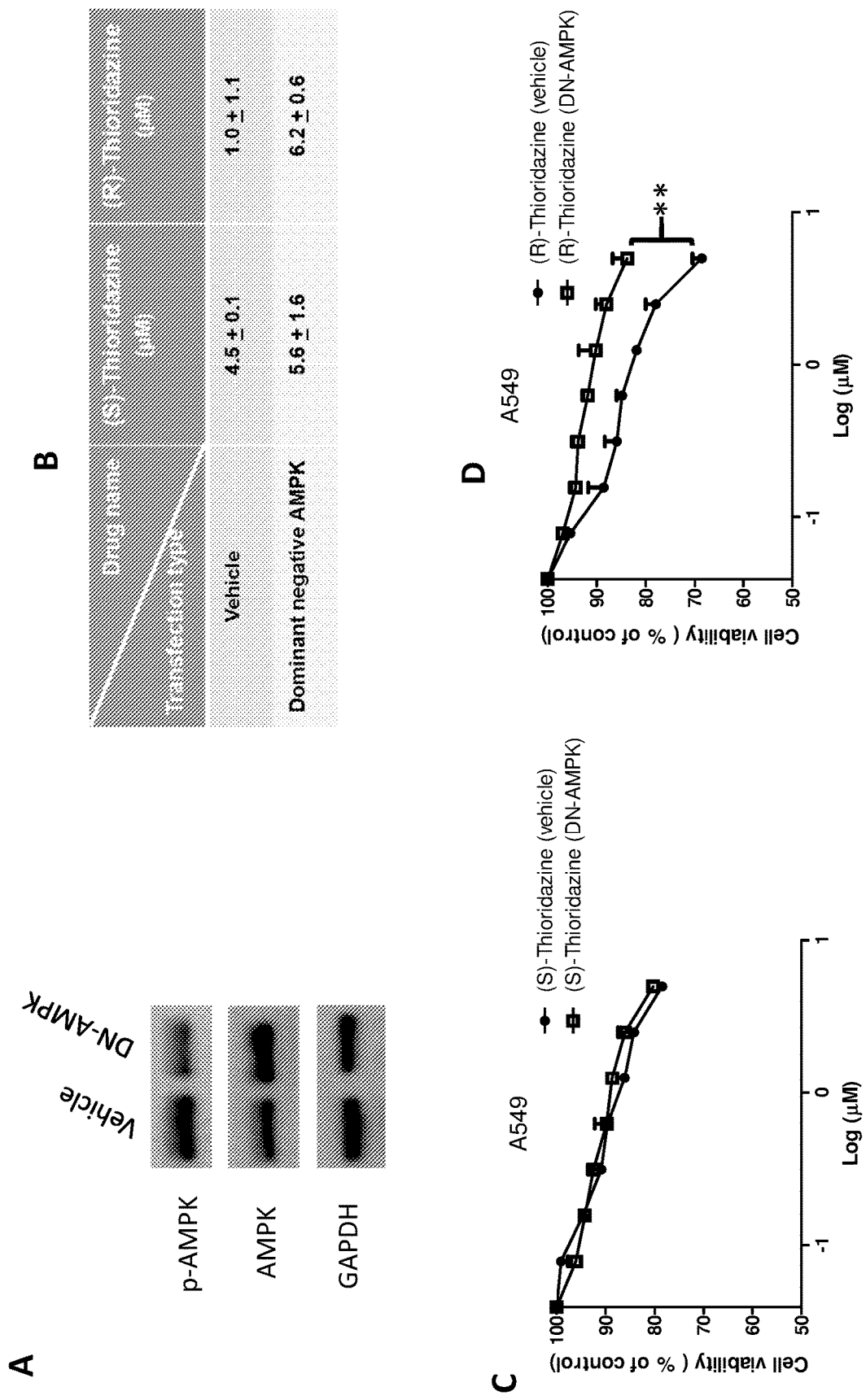
FIGS. 12A-D illustrate the ability of thioridazine in inhibiting the viability of A549 through AMPK activation.

Having unexpectedly found that thioridazine and its enantiomers each possess anti-cancer property, we set forth to discover mechanisms responsible for the anti-cancer property. To increase the efficiency for identifying the anti-cancer mechanism, we used microarray profiles to explore differences in gene expression and pathways between each single enantiomers as well as racemic form of thioridazine. The microarray profile results unexpectedly revealed that thioridazine and its enantiomers each inhibit cholesterol synthesis-related enzymes, e.g. HMG-CoA reductase. (See FIGS. 7A-D as well as Examples) Further experimentation revealed that, by activating AMPK, thioridazine and its enantiomers are each able to inhibit the activity of HMG-CoA reductase. In addition, the results show that (S)-thioridazine is a better AMPK activator at lower concentrations than (R)- or racemic form of thioridazine. (See FIGS. 8, 9A-B, and 15E as well as Examples) To further confirm thioridazine as an AMPK activator, A549 cells were transfected with dominant negative AMPK (DN-AMPK), followed by thioridazine treatment. FIG. 12A shows dominant negative AMPK suppressed AMPK activity as showed by reducing p-AMPK level. Moreover, blockade of AMPK activity reduced (S)-thioridazine, but not (R)-thioridazine, cytotoxicity in A549 cells (FIG. 12B-D). Using thioridazine's AMPK activating property as a guide, we conducted further experimentation to determine that KRAS mutant cells are more sensitive to the AMPK activator than KRAS wild-type cells or any other mutations frequently observed in the NSCLC cells. In particular, (S)-thioridazine was much more effective than (R)- or racemic form of thioridazine in this regard. (See FIGS. 10A-C, 11A-D and 12A-D as well as Examples) Therefore, one embodiment of the invention provides use of (S)- or (R)-thioridazine in the manufacture of medicament for treating NSCLC with KRAS mutation.

Accordingly, further provided in the invention is a method for treating NSCLCs with KRAS mutation comprising administering to a subject a therapeutically effective amount of (S)- or (R)-thioridazine enantiomer. Furthermore, an embodiment of the present invention provides for a pharmaceutical composition comprising (S)- or (R)-thioridazine for treating NSCLC with KRAS mutation.

In addition, since it was unexpectedly found the relationship between KRAS mutations and cholesterol biosynthesis in lung cancer, the KRAS mutation could be exploited for patient selection in clinical trials. Therefore, an embodiment of the present invention provides for a method for selecting clinical trial subjects for (S)- or (R)-thioridazine for treating NSCLC comprising the step of selecting clinical trial subjects who are afflicted with NSCLC with KRAS mutation.

Aside from anti-cancer experiments, we also conducted experiments to determine severity of catalepsy by thioridazine and its enantiomers. Therefore, in vivo toxicity studies were conducted to determine likelihood of each forms of thioridazine in causing catalepsy, one of the major well-known side effects of thioridazine in humans. Results of the studies are shown in FIG. 16.

As shown in FIG. 16, (S)-thioridazine in the table is clearly less toxic with regards to causing catalepsy than (R)-thioridazine as well as racemic form of thioridazine. Accordingly, the invention provides use of (S)-thioridazine enantiomer in treating cancer and in reducing drug resistance of a cancer with substantially lower risk of catalepsy than if other forms of thioridazine were used.

In addition, it was unexpectedly found that each of (S)-thioridazine or (R)-thioridazine in combination with an existing anti-cancer drugs such as cisplatin and pemetrexed result in synergistic effect in inhibiting the growth of cancer tumors in vitro and in vivo. (See FIGS. 13A-B, 15A-D and FIG. 17 as well as Examples) Unexpectedly, (S)-thioridazine achieved higher synergy than (R)-thioridazine or thioridazine. (See FIG. 13B and Examples) Therefore, one embodiment of the invention provides for use of (S)- or (R)-thioridazine in combination with an anti-cancer drug for the manufacture of a medicament for treating cancer by inhibiting the growth of cancer tumors.

Accordingly, further provided in the invention is a method for treating cancer by inhibiting the growth of cancer tumors comprising administering to a subject a therapeutically effective amount of (S)- or (R)-thioridazine in combination with an anti-cancer drug such as cisplatin, pemetrexed, gefitinib and gemcitabin, wherein the anti-cancer drug is administered to the subject before, simultaneously with or after the administration of the (S)- or (R)-thioridazine. Furthermore, one embodiment of the present invention provides a pharmaceutical composition comprising (S)- or (R)-thioridazine in combination with an anti-cancer drug for inhibiting the growth of cancer tumors, wherein the pharmaceutical composition may be formulated as one single formulation or multiple formulations.

Moreover, it was also unexpectedly found that each of racemic thioridazine, (S)-thioridazine or (R)-thioridazine in combination with existing anti-cancer drugs such as pemetrexed and gefitinib result in synergistic effect in overcoming drug resistance in vitro. (See FIGS. 14A-C as well as Examples) Unexpectedly, (S)-thioridazine achieved higher synergy than (R)-thioridazine or thioridazine. (See FIGS. 14A-C as well as Examples) Therefore, one embodiment of the invention provides for use of (S)- or (R)-thioridazine in combination with an anti-cancer drug for the manufacture of a medicament for treating cancer by overcoming drug resistance.

Accordingly, further provided in the invention is a method for treating cancer by overcoming drug resistance comprising administering to a subject a therapeutically effective amount of (S)- or (R)-thioridazine in combination with an anti-cancer drug such as cisplatin or pemetrexed, wherein the anti-cancer drug is administered to the subject before, simultaneously with or after the administration of the (S)- or (R)-thioridazine. Furthermore, one embodiment of the present invention provides a pharmaceutical composition for treating cancer by overcoming drug resistance comprising (S)- or (R)-thioridazine in combination with an anti-cancer drug, wherein the pharmaceutical composition may be formulated as one single formulation or multiple formulations.

In the present invention, the active ingredient may be administered in any route that is appropriate, including but not limited to parenteral or oral administration. The compositions for parenteral administration include solutions, suspensions, emulsions, and solid injectable compositions that are dissolved or suspended in a solvent immediately before use. The injections may be prepared by dissolving, suspending or emulsifying one or more of the active ingredients in a diluent. Examples of said diluents are distilled water for injection, physiological saline, vegetable oil, alcohol, and a combination thereof. Further, the injections may contain stabilizers, solubilizers, suspending agents, emulsifiers, soothing agents, buffers, preservatives, etc. The injections are sterilized in the final formulation step or prepared by sterile procedure. The pharmaceutical composition of the invention may also be formulated into a sterile solid preparation, for example, by freeze-drying, and may be used after sterilized or dissolved in sterile injectable water or other sterile diluent(s) immediately before use.

The present invention is further illustrated by the following examples, which are provided for the purpose of demonstration rather than limitation.

EXAMPLES—TRIFLUOPERAZINE

I. Materials and Methods
Cell Culture, Chemicals, and Clonogenic Assay

The NSCLC cancer cell lines, A549, H1975, CL25, CL83, CL97, CL141, and CL152 were maintained in RPMI medium. Tested cells were seeded respectively in 6 well plates with $10^4$ cells per well for 14 days. Each well contained 10 ml RPMI medium as cultured condition for NSCLC cells. Trifluoperazine, chlorpromazine, thioridazine, triflupromazine, and promazine were purchased from Sigma and perphenazine was from Prestwick Chemical. Trifluoperazine and other tested drugs were added 24 hours after seeding of the cells. The medium and tested drugs were changed once on day 4. After the treatments, cells were washed with PBS, and the colonies were fixed with fix solution (acetic acid:methanol=1:3) and stained with 0.5% crystal violet in methanol. After removing the crystal violet carefully and rinse with tap water, the colonies were counted manually.

Side Population Analysis and Purification Using Flow Cytometry

Single-cell suspensions of cells were detached from dishes with Trypsin-EDTA (Invitrogen) and suspended at $1 \times 10^6$ cells/mL in Hank's balanced salt solution (HBSS) supplemented with 3% fetal calf serum and 10 mM Hepes. These cells were then incubated at 37° C. for 90 minutes with 20 µg/mL Hoechst 33342 (Sigma Chemical, St. Louis, Mo.), either alone or in the presence of 50 µM verapamil (Sigma), an inhibitor of the verapamil-sensitive ABC transporter. After 90 minutes incubation, the cells were centrifuged immediately for 5 minutes at 300 g and 4° C. and resuspended in ice-cold HBSS. The cells were kept on ice to inhibit efflux of the Hoechst dye, and 1 µg/mL propidium iodide (BD) was added to discriminate dead cells. Finally, these cells were filtered through a 40 µm cell strainer (BD) to obtain single-suspension cells. Cell dual-wavelength analysis and purification were performed on a dual-laser FACS Vantage SE (BD). Hoechst 33342 was excited at 355 nm UV light and emitted blue fluorescence with a 450/20 band-pass (BP) filter and red fluorescence with a 675 nm edge filter long-pass (EFLP). A 610 nm dichroic minor short-pass (DMSP) was used to separate the emission wavelengths. PI-positive (dead) cells were excluded from the analysis.

Soft Agar Assay

Freshly sorted CL141 side population (SP) and non-side population (NSP) cells were counted and plated in triplicate at 200 cells per well in six-well plates coated with 1% agarose. Anchorage-independent growth was assessed after incubation for 10-14 days in culture media with or without trifluoperazine (0, 5 and 10 µM), which was replaced every 4 days. Plates were stained with 0.005% crystal violet, and the colonies were counted manually under a microscope and photographed.

Tumor Spheroid Assay

For the formation of tumor spheroids, cells were cultured in HEScGRO serum-free medium (human) (Chemicon) supplemented with 20 ng/mL hEGF, 20 ng/mL bFGF and NeuroCult NS-A proliferation supplements. Cells were seeded at low densities (1000 cells/mL) in 12-well low adhesion plates at 1 mL per well. Spheroids (tight, spherical, nonadherent masses >90 µm in diameter) were counted, and at least 50 spheroids per group were measured with an ocular micrometer. For secondary spheroid-forming assays, primary spheroids were dissociated mechanically and processed as in the primary assay. For the quantification of the percentage of spheroid-forming cells, cells were seeded at one cell per well in 96-well plates.

Reporter Assay

Spheroid cells were plated in 6-well plates, grown to 80%-90% confluence, and transiently transfected with 1.8 µg TOPflash or FOPflash plasmids using Lipofectamine TOPflash contains 3 copies of the Tcf/Lef binding sites upstream of a thymidine kinase (TK) promoter and the firefly luciferase gene. FOPflash contains mutated copies of the Tcf/Lef sites and is used as a control for measuring nonspecific activation of the reporter. To normalize for transfection efficiency, cells were cotransfected with 0.2 µg of the internal control reporter encoding *Renilla reniformis* luciferase driven by the TK promoter. After transfection, cells were incubated in medium with or without trifluoperazine (0-10 µM) for 48 hrs and then lysed with reporter lysis buffer after harvest. Luciferase activity was determined by the Luciferase Assay System (Promega) using a Microplate Luminometer (Berthold). The experiments were performed in triplicate, and the results were reported as fold induction compared with the control group after transfection efficiency normalization.

ALDEFLUOR Assay

High aldehyde dehydrogenase (ALDH) enzyme activity was used to detect lung CSC populations in this study. The ALDEFLUOR assay was performed according to the manufacturer's guidelines (StemCell Technologies). Briefly, single cells obtained from cell cultures were incubated in an ALDEFLUOR assay buffer containing an ALDH substrate (bodipy-aminoacetaldehyde, BAAA) for 50 minutes at 37° C. As a negative control, a fraction of cells from each sample was incubated under identical conditions in the presence of an ALDH inhibitor (diethylaminobenzaldehyde, DEAB). Flow cytometry was used to measure the ALDH-positive cell population.

Western Blotting Analysis

Cells were lysed in lysis buffer (50 mM Tris-HCl, pH 7.4, 5 mM $MgCl_2$, 1% Nonidet P-40, 150 mM NaCl, 1 mM phenylmethylsulfonyl fluoride). Total protein was isolated and subjected to SDS polyacrylamide gel electrophoresis and electrotransfered onto PVDF membranes (Millipore). Primary antibodies Bax, Bak, Bcl-2, XIAP, Mcl-1, Cleaved caspase-9, caspase-3, PARP, c-Myc, CD44, cyclin D1 were obtained from Cell Signaling, Met was purchased from Santa Cruz and CD133 was from Miltenyi Biotec, and secondary antibodies for anti-mouse and anti-rabbit horseradish peroxidase (HRP)-conjugation were from Chemicon International. The protein detection was performed with enhanced chemiluminescence (ECL™) method captured by a Luminescence Imaging System (LAS-4000™, Fuji Photo Film Co., Ltd).

Generation of a Stable Dual Reporter-Expressing Lung Cancer Cell Line

The dual optical reporter system L2G fusion construct (firefly luciferase 2 and eGFP) was a generous gift from Dr. Gambhir, Stanford University. Stable L2G-expressing CL97 cells were generated accordingly. Briefly, CL97 cells with stable integration of the L2G reporter were generated by lentiviral-mediated gene transfer. 293FT cells were transfected with the lentiviral vector L2G, the packaging plasmid pCMVΔ8.74 and the envelope plasmid pMD2.G (Nat Biotechnol 1997; 15:871-875). The target CL97 cells were infected with the viral particles and selected using Zeocin. CL97 cells carrying the L2G reporter system (CL97-L2G) were obtained and expanded for further experiments.

Evaluation of Trifluoperazine's Anti-CSC Effects Using Non-Invasive Bioluminescent Imaging NOD/SCID mice were purchased from National Taiwan University and maintained in compliance with the institutional policy. All animal procedures were approved by the IACUC (Institutional Animal Care and Use Committee) at Taipei Medical University.

For bulk lung tumor model, CL97-L2G cells were intravenously administered into the animals via tail vein at a concentration of $1\times10^6$ cells/100 μl PBS. One week post tumor injection, different treatment regimens were started. Four regimens were performed, trifluoperazine (5 mg/kg/day), gefitinib (150 mg/kg/day, oral gavage) and a combination of trifluoperazine (5 mg/kg/day i.p injection)+gefitinib (100 mg/kg/day, oral gavage) for a period of 4 weeks.

To examine the preventive and anti-CSC effects of trifluoperazine, CL97-L2G spheroids were pre-treated with trifluoperazine (5 μM, <IC50, overnight), re-suspended from their spheroid form and orthotopically injected into the lungs of NOD/SCID mice ($1\times10^4$ cells/50 μL matrigel/inoculation). The animals did not receive further treatment for the span of the experiment. CL97-L2G-bearing mice (both bulk lung tumor and CSC models) were imaged weekly using the IVIS 200 system (Caliper Life Sciences). Data are expressed as fold change in total photon flux/initial total photon flux and were analyzed using Living Image 1.0 software (Caliper Life Sciences). Mice were humanely sacrificed at the end of experiments and lung tumor biopsies were obtained for further analysis.

II. Results

Trifluoperazine Inhibited Proliferation and Induced Apoptosis of Gefitinib-Resistant NSCLC Cells We hypothesized that trifluoperazine would inhibit tumor growth and overcome drug resistance by exerting anti-CSC effects. In addition to the commonly used cell lines (A549 and H1975), we also established several cell lines including CL83, CL141, CL152, CL25, and CL97 cell lines which were isolated from the pleural effusion of NSCLC patients at the National Taiwan University Hospital. The investigation was approved by the Institutional Review Board of the National Taiwan University Hospital. Informed consent was obtained before pleural effusion was collected. A summary of the main features of these cell lines, including their histological and mutational characteristics, as well as whether they have intrinsic or acquired resistance to EGFR TKIs, is provided in FIG. 18. We demonstrated that trifluoperazine dose-dependently inhibited NSCLC cell growth, and the respective IC50 values (48 hrs incubation) for CL83, CL141, CL152, CL25, CL97, and H1975 were 14, 8.5, 12, 13, 7.2, and 15 μM, respectively (FIG. 19 and FIG. 1).

Among these cell lines, we chose CL141, an adenocarcinoma with wild-type EGFR status which shows resistance to gefitinib, as a representative target cell line for apoptosis analysis. Annexin V/PI staining was performed after treatment with different dosages of trifluoperazine. Both early and late apoptotic cells were counted. After 48 hrs, trifluoperazine-treated CL141 cells exhibited a dose-dependent increase in Annexin V-positive cells when compared to the control cells (FIG. 1B). The results indicated that trifluoperazine inhibited the proliferation of and induced apoptosis of gefitinib-resistant NSCLC cells.

Trifluoperazine Reduced the Percentage of and Induced Apoptosis of Lung CSCs

We selected gefitinib-resistant cell lines CL83, CL141, CL152 (with wild-type EGFR) and CL97 (harboring EGFR-G719A+T790M mutations) and isolated their CSCs using side-population method (1.54%, 2.13%, 1.95%, and 1.9% of the side population cells, respectively). After treatment with 5 μM trifluoperazine, the percentage of side population cells significantly decreased (FIG. 1C).

For further clarification, we examined if trifluoperazine treatment could deplete the percentage of the cells with ALDH expression, an established marker for both hematopoietic and NSCLC CSCs. CL141 (adenocarcinoma) and CL152 (squamous cell carcinoma) were selected as representative target NSCLC cell lines. Trifluoperazine treatment decreased the ALDH+CL141 cell population from 4.31% to 0.84%, and from 3.73% to 1.08% in CL152 cells (FIG. 1D).

To investigate the apoptotic-associated signal transduction in lung CSC after trifluoperazine treatment, CL97 (adenocarcinoma with EGFR-T790M-acquired resistance mutation) was selected as a target cell line. After trifluoperazine treatment of CL97 cancer spheroids, Bax, Bak, cleaved PARP, caspase-3, and caspase-9 was increased dose-dependently, whereas anti-apoptotic Bcl-2, XIAP, and Mcl-1 were decreased (FIG. 1E).

Figure 2:
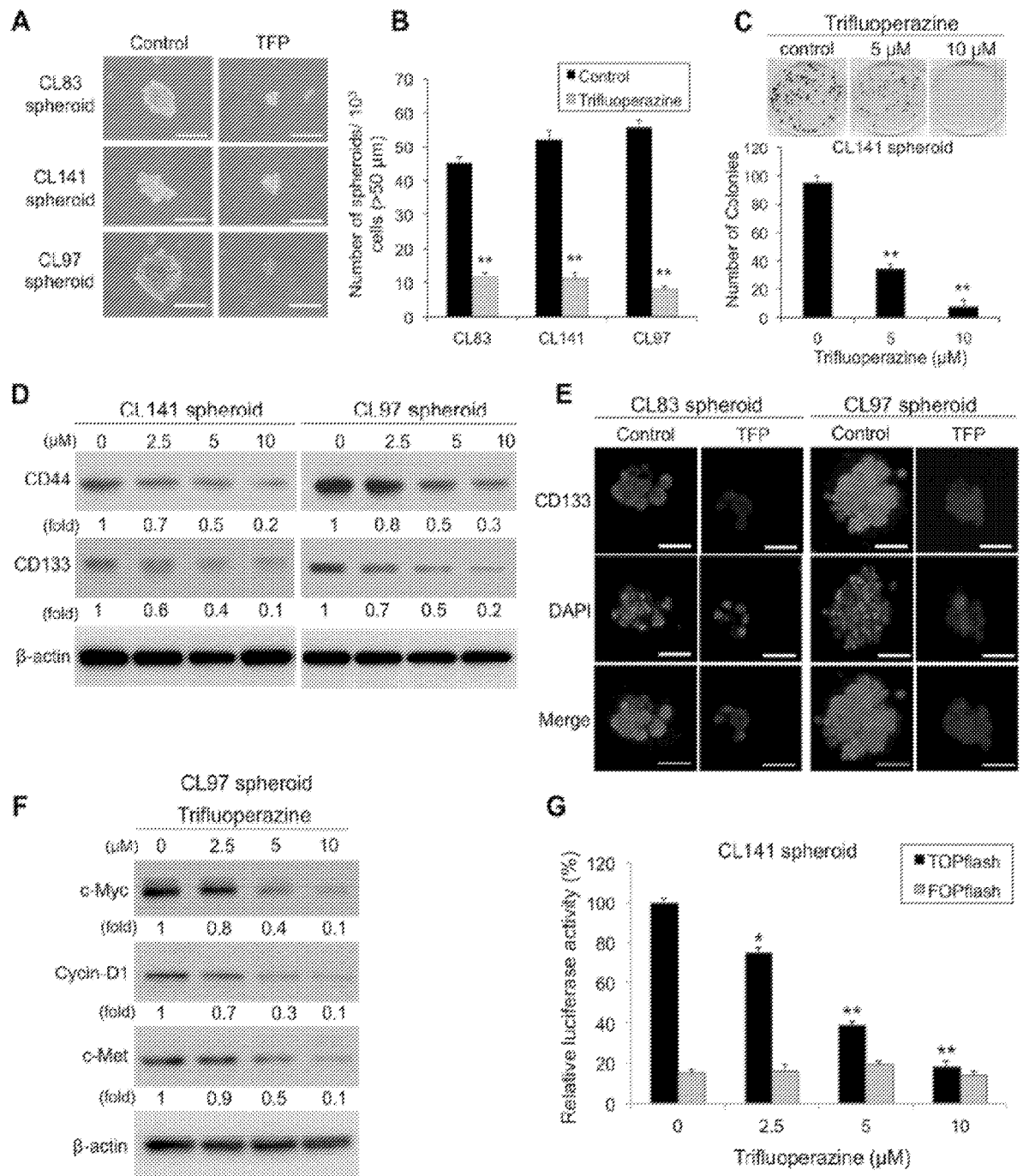
FIGS. 2A-G provide the effects of trifluoperazine in inhibiting the capacity of lung cancer spheroid self-renewal, wherein FIGS. 2A and 2B respectively show the size and the number of CL83, CL141 and CL97 spheroids after treatment with trifluoperazine for 48 hrs (N=3,  $P<0.01$)

Trifluoperazine Inhibited the Clonogenicity and Stemness-Associated Markers of Lung CSCs Three different gefitinib-resistant lung CSCs, including CL141 (wild-type EGFR), CL83 (wild-type EGFR) and CL97 (EGFR-G719A+T790M acquired resistance mutation) were treated with trifluoperazine to examine its effects on tumor spheroid formation. Trifluoperazine dose-dependently decreased the size and number in all spheroids (FIGS. 2A, 2B, and 2C). The mean colony formation of CL141 spheroids on soft agar decreased after 12 days of treatment with either 5 or 10 μM trifluoperazine (FIG. 2C, mean colony number, control: 92, 5 μM: 32, 10 μM: 8). CL141 and CL97 spheroids were treated with increasing dosages of trifluoperazine (0, 2.5, 5, and 10 μM) for 48 hrs. Two established lung CSC markers, CD44 and CD133, were dose-dependently down-regulated by trifluoperazine as measured by Western blotting and immunochemical staining (FIGS. 2D and E).

To explore the molecular mechanisms mediated by trifluoperazine, CL97 spheroids were treated with trifluoperazine and analyzed by western blots. Wnt/β-catenin signaling downstream targets, Cyclin D1 and c-Myc, and c-Met were decreased by trifluoperazine (FIG. 2F). Additionally, trifluoperazine (at low concentration, 2.5 μM) inhibited TCF-mediated transcription in CL141 spheroids disrupted spheroid formation (FIG. 2G).

Figure 3:
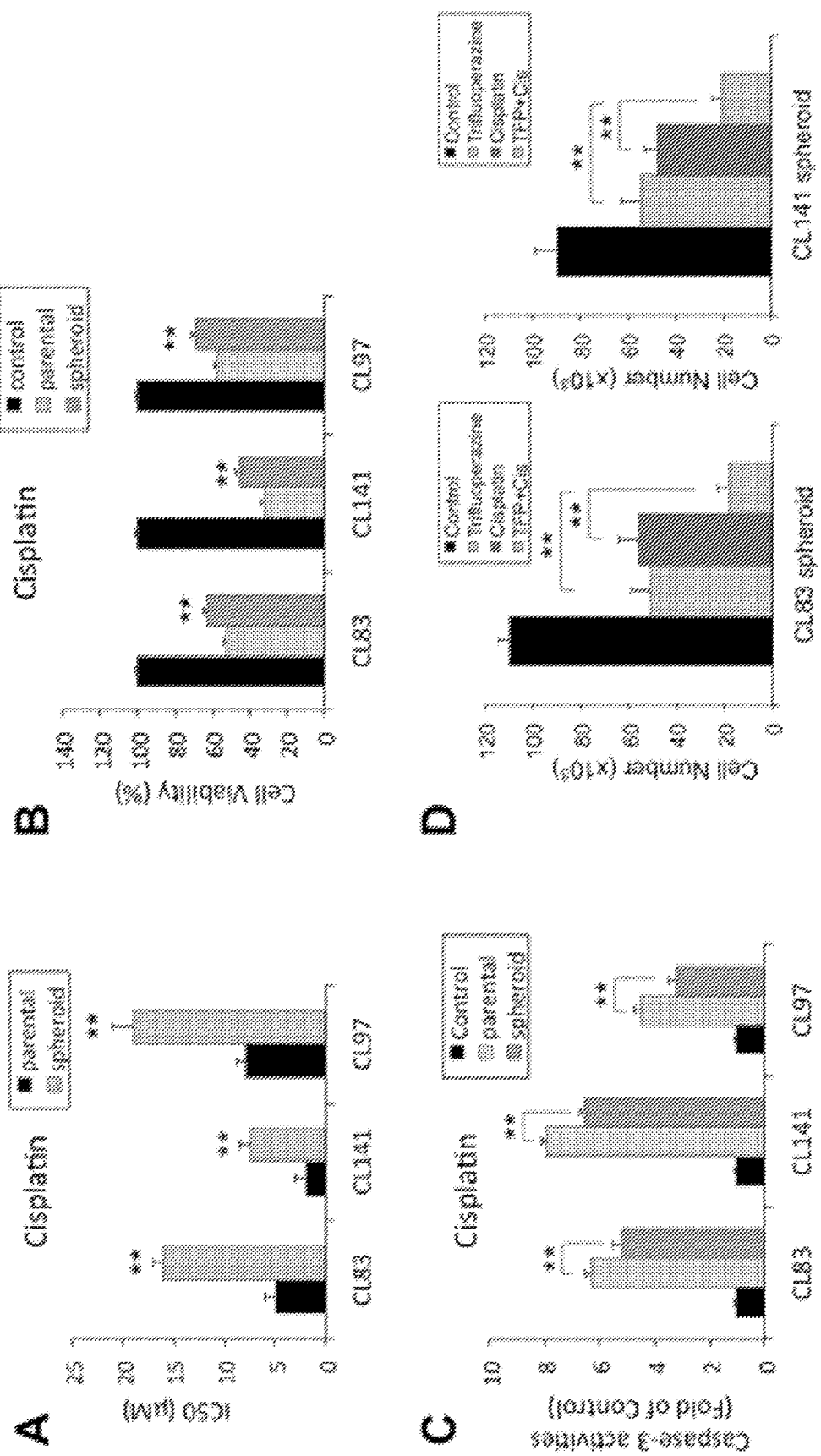
Figure 3:
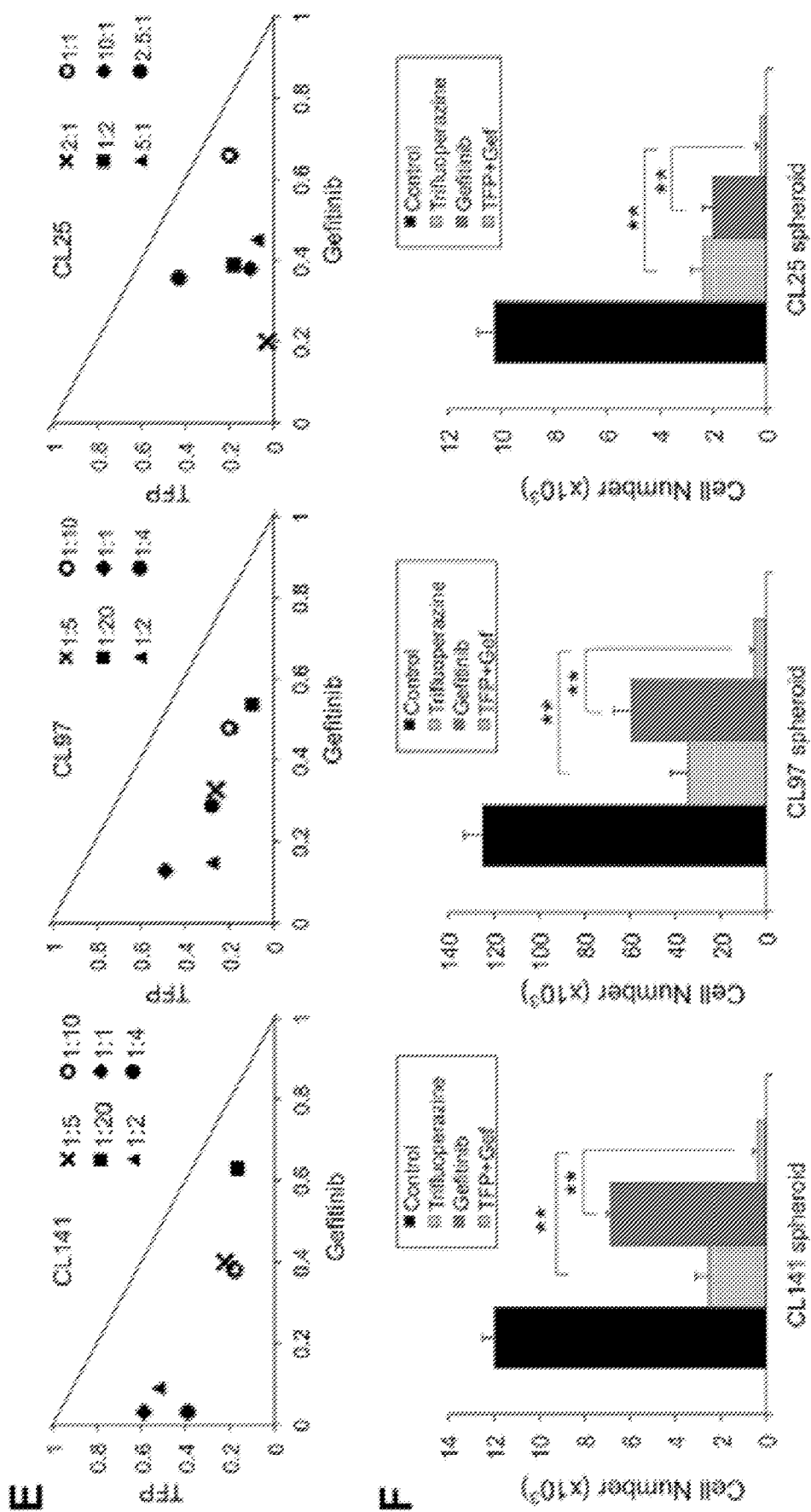
Figure 3:
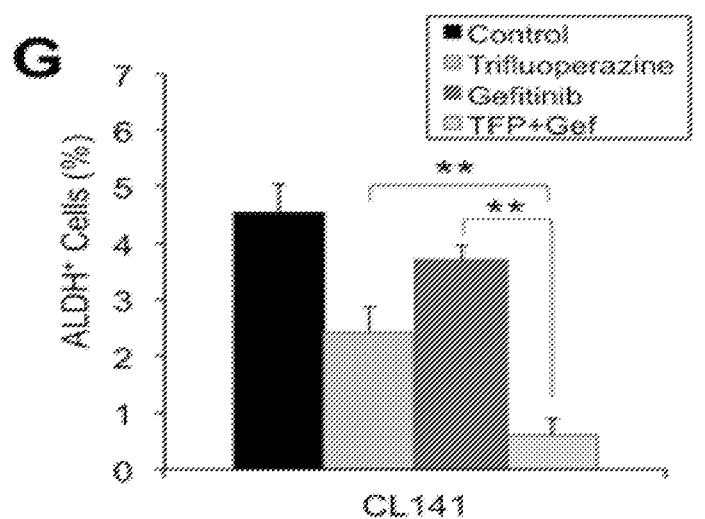
Figure 3:
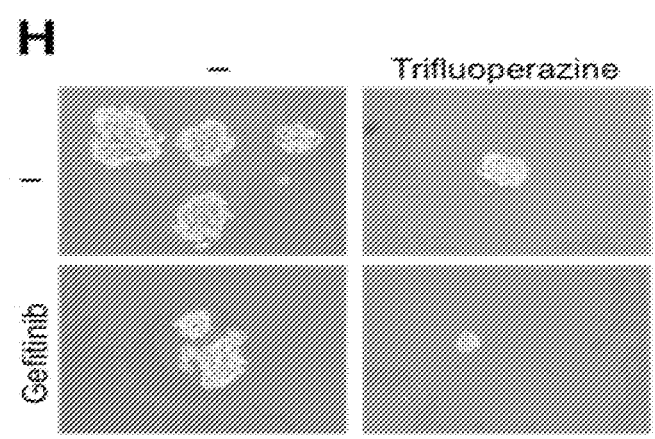

Trifluoperazine Synergistically Inhibits Lung CSCs In Vitro while Combined with Cisplatin or Gefitinib We selected three gefitinib-resistant NSCLC cell lines, CL141 (wild type EGFR), CL83 (wild type EGFR) and CL97 (EGFR-G719A+T790M acquired resistant mutation) to determine if trifluoperazine could sensitize these cells towards chemotherapeutic agents. While treating with 10 μM of cisplatin for 24 hrs, all CL141, CL83 and CL97 spheroids showed a significantly higher IC50 (FIG. 3A) than their parental cells. Under the same condition, all spheroids showed higher viability and a lower caspase-3 activity as compared to their parental cells (FIGS. 3B and 3C).

Next, we examined whether trifluoperazine could enhance the cytotoxic effects of cisplatin or gefitinib. The combined trifluoperazine and cisplatin treatment provided a significantly higher cytotoxic effect in both CL83 and CL141 spheroids than either trifluoperazine or cisplatin treatment alone (FIG. 3D).

Assessment of the combinatorial activity of trifluoperazine and gefitinib was performed using the isobolographic method (Chou T C and Talalay P. *Adv Enzyme Regul* 1984; 22:27-55). Values below the line are synergistic, whereas those close to the line are additive and those above the line antagonistic. The synergistic activity of both agents was demonstrated from the normalized isobolograms obtained from the EGFR-wide-type cells (CL141), EGFR-G719A+T790M mutation cells (CL97) and EGFR-exon 19 deletion cells (CL25) (FIG. 3E). The enhanced cytotoxicity was also observed in all CL141, CL97 and CL25 spheroids. To investigate the effect of trifluoperazine on gefitinib therapy, CL25 (EGFR-TKI sensitive cell line) spheroids growth inhibition assay was performed as a positive control. CL25 spheroids were exposed to individual agents or a combination of trifluoperazine with gefitinib, as well as CL141 and CL97 cell lines (FIG. 3F). Gefitinib alone effectively suppressed the spheroid formation in CL25 but significantly less in CL141 and CL97 cells. The combination of trifluoperazine and gefitinib significantly suppressed the spheroid formation of CL141 and CL97. These observations indicated that the addition of trifluoperazine sensitized gefitinib-resistant lung cancer cells. In addition, the percentage of ALDH+ CL141 cells was moderately decreased at 10 µM of trifluoperazine. However, an enhanced inhibitory effect was observed when trifluoperazine was combined with 5 µM of gefitinib (FIG. 3G). A similar enhanced inhibition on CL141 spheroid formation was observed (FIG. 3H).

Trifluoperazine Treatment Suppressed Tumorigenesis of Gefitinib-Resistant CL97-L2G in Mouse Lung Cancer Models NOD/SCID mice bearing gefitinib-resistant CL97-L2G (G719A+T790M acquired resistance mutation) cells were used to evaluate the anti-tumor effects of trifluoperazine. First, CL97 bulk tumor cells were injected intravenously into the tail vein of NOD/SCID mice that subsequently received vehicle with trifluoperazine alone (5 mg/kg/day, i.p), gefitinib alone (150 mg/kg/day, oral gavage), or a combination of trifluoperazine (5 mg/kg/day, i.p) and gefitinib (100 mg/kg/day, oral gavage) treatment. Comparatively, mice that received trifluoperazine alone showed significantly lower tumor burden than those that received vehicle and gefitinib alone (FIG. 4A). As expected, gefitinib-treated mice demonstrated a similar level of tumor burden as the vehicle control group. Mice that received the gefitinib/trifluoperazine combined treatment exhibited the lowest tumor burden. Tumor burden was measured and quantified based on the fold change in bioluminescence intensity.

In the prevention experiment, CL97-L2G cells were pretreated with vehicle or trifluoperazine (5 µM, <IC50) and orthotopically implanted into NOD/SCID mice. Mice that received the trifluoperazine-pretreated CL97-L2G cells exhibited delayed and significantly reduced in-situ tumor growth as compared to vehicle-treated control (FIG. 4B). To explore the molecular mechanisms mediated by trifluoperazine, total protein lysates were harvested from tumor samples. The expression level of stemness molecules including c-Myc and β-catenin was found to be decreased. Cyclin D1 expression was also suppressed by both trifluoperazine and the combined treatment while the activated form of caspase-3 was increased by both trifluoperazine and the combined treatment (FIG. 4C). Gefitinib treatment did not significantly influence the expression level of either c-Myc or β-catenin.

Thioridazine and Thioridazine Enantiomers

I. Materials and Methods

Side Population Analysis and Purification Using Flow Cytometry

Single-cell suspensions of cells were detached from dishes with Trypsin-EDTA (Invitrogen) and suspended at $1 \times 10^6$ cells/mL in Hank's balanced salt solution (HBSS) supplemented with 3% fetal calf serum and 10 mM Hepes. These cells were then incubated at 37° C. for 90 minutes with 20 µg/mL Hoechst 33342 (Sigma). The ABC transporter inhibitor, verapamil (Sigma), was added at a final concentration of 50 µM to confirm the gating area on flow cytometry. After a 90-minute incubation with the indicated drugs, the cells were centrifuged immediately for 5 minutes at 300 g and 4° C. and resuspended in ice-cold HBSS. The cells were kept on ice to inhibit efflux of the Hoechst dye, and 1 µg/mL propidium iodide (PI, BD) was added to discriminate dead cells. Finally, these cells were filtered through a 40 µm cell strainer (BD) to obtain single-suspension cells. Cell dual-wavelength analysis and purification were performed on a dual-laser FACS Vantage SE (BD). Hoechst 33342 was excited at 355 nm UV light and emitted blue fluorescence with a 450/20 band-pass (BP) filter and red fluorescence with a 675 nm edge filter long-pass (EFLP). A 610 nm dichroic mirror short-pass (DMSP) was used to separate the emission wavelengths. PI-positive (dead) cells were excluded from the analysis.

ALDEFLUOR Assay

High aldehyde dehydrogenase (ALDH) enzyme activity was used to detect lung cancer stem cell populations. The ALDEFLUOR assay was performed according to the manufacturer's guidelines (StemCell Technologies). Briefly, single cells obtained from cell cultures were incubated in an ALDEFLUOR assay buffer containing an ALDH substrate (bodipy-aminoacetaldehyde, BAAA) for 50 minutes at 37° C. As a negative control, a fraction of cells from each sample was incubated under identical conditions in the presence of an ALDH inhibitor (diethylaminobenzaldehyde, DEAB, from StemCell Technologies). Flow cytometry was used to measure the ALDH-positive cell population Tumor Spheroid Assay In brief, single cells were plated in 24-well ultralow attachment plates (Corning Inc.) at a density of 1,000 cells/mL in tumor spheroid culture medium, which consists of DMEM/F12 supplemented with 1% N2 Supplement (Invitrogen), 20 ng/mL basic fibroblast growth factor (Sigma-Aldrich), and 20 ng/mL epidermal growth factor (Invitrogen) with 1% penicillin/streptomycin (Invitrogen), at 37° C. in a humidified atmosphere of 95% air and 5% CO2. Cells were cultured twice per week. When cells were passaged, tumor spheres were harvested. Spheroids were dissociated with TrypLE™ (Invitrogen). Spheroid cells were counted using the Trypan Blue Exclusion method.

Clonogenic Assay

Tested cells were seeded respectively in 6 well plates with $10^3$ cells per well for 5 to 7 days. Thioridazine and its enantiomers were added 24 hrs after seeding of the cells. The medium and tested drugs were changed every 4 days. After the treatments, cells were washed with PBS, and the colonies were fixed with fix solution (3.7% formaldehyde) and stained with 0.5% crystal violet in methanol. After removing the crystal violet carefully and rinse with tap water, the colonies were counted manually. Each experiment was performed independently at least 2 times in triplicate and cytotoxicitiesare given as means±SD.

Western Blotting

To obtain total cell lysate, cells were lysed in RIPA buffer (50 mM Tris-HCl, pH 7.4, 150 mM NaCl, 1 mM phenylmethylsulfonyl fluoride, 5 mM $MgCl_2$ and 1% NP-40) supplemented with protease and phosphatase inhibitor cocktail tablets (Roche Diagnostics AB, Stockholm, Sweden). Lysates (30 μg) were resolved by SDS-PAGE and electrotransferred onto PVDF membrane (Millipore). Immunoblotting was performed with various primary antibodies, and secondary antibodies for anti-rabbit and anti-mouse horseradish peroxidase (HRP)-conjugation were from Chemicon International. The protein detection was performed with chemiluminescence (ECL™) method captured by a Luminescence Imaging System (LAS-4000™, Fuji Photo Film CO., Ltd).

HMG-CoA Reductase (HMGCR) Activity Determination Assay

Principle of the Assay Reaction scheme:

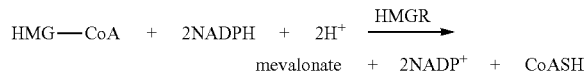

The assay is based on a spectrophotometric measurement of the decrease in absorbance, which represents the oxidation of NADPH by the catalytic subunit of HMGCR in the presence of the substrate HMG-CoA (purchased from sigma, catalog number: CS1090). Thioridazine and its enantiomers were incubated with the catalytic subunit of HMGCR in 96 well with 0.01 μM, 0.1 μM, 1 μM and 5 μM, respectively.

The Transfection of the Dominant Negative AMPK Plasmid

Cells were seeded at the density of 6000/well at 48-well. After 16-24 hrs, the A549 cells were transfected with the dominant negative AMPK plasmid (AMPKα1 recombinant adenovirus expresses HA-tagged human α1 subunit with a D159A mutation in the ATP binding domain) for 16~24 hrs. The cells were further treated with the thioridazine from 0.1 μM to 5 μM for 48 hrs and the viability was determined via SRB assay.

The Transfection of the $KRAS^{G12D}$ Plasmid

Cells were seeded at the density of 6000/well at 48-well. After 16~24 hrs, the A549 cells were transfected with the pLenti-$KRAS^{G12D}$-EGFP plasmid for 16~24 hrs. The cells were further treated with the thioridazine from 0.1 μM to 5 μM for 48 hrs and the viability was determined via SRB assay Xenograft Mouse Model for In Vivo Evaluation of Thioridazine All the animal experiments were performed strictly under the Affidavit of approval of animal use protocol (LAC-2013-0086), Taipei Medical University. NSCLC cells, H441, expressing dual reporter system (GFP and firefly luciferase) were subcutaneously ($1 \times 10^6$ cells per injection) implanted in the right flank of NOD/SCID mice (6 weeks old, purchased from BioLASCO CO., Ltd, Taiwan). Animals were subjected to bioluminescence imaging (IVSI 200, PerkinElmer, Waltham, Mass.) one week post tumor inoculation to ascertain approximately equal tumor growth in all animals. Subsequently, animals were randomly divided into different groups and treatments were initiated. The tumor burden was recorded and compared according to the change in bioluminescence intensity. The tumor burden was represented by the following formula: fold change in bioluminescence (bioluminescence intensity n/bioluminescence intensity, where n=number of week, and 0=starting bioluminescence intensity). At the end of the experiment, mice were humanely sacrificed and tumor biopsies from each group were collected for further analyses. In later trials, tumor volume was measured using a caliper and the volume was calculated using the following formula: Volume=[length× $width^2$]/2. The change in tumor size was expressed as the fold change in volume (with respect to the same tumor). The fold change in tumor burden each week was calculated as fold change=(week)n/tumor size initial (week 1). At the end of experiment, mice were sacrificed and tumor samples from each group were collected at the end of experiment for further analyses.

Assay Catalepsy

1. Test Substance and Dosing Pattern

Thioridazine enantiomers (S)-thioridazine, (R)-thioridazine and thioridazine provided by National Research Program for Biopharmaceuticals, were dissolved in 0.9% NaCl and were administered intravenously (IV) at 1 mL/kg and intraperitoneally (IP) at 5 mL/kg.

The formulations are summarized as follows:

| Test Compound | Vehicle | Solubility[a] | Color | Light Protection[b] | Temperature[c] | Formulation mg/mL |
|---|---|---|---|---|---|---|
| ([S]R)-Thioridazine | 0.9% NaCl | S | Colorless | Y | RT | 0.1, 0.3, 1, 3 for IV 0.06, 0.2 and 0.6 for IP |
| ([R]S)-Thioridazine | 0.9% NaCl | S | Colorless | Y | RT | 0.1, 0.3, 1, 3 for IV 0.06, 0.2 and 0.6 for IP |
| Thioridazine | 0.9% NaCl | S | Colorless | Y | RT | 0.1, 0.3, 1, 3 for IV 0.06, 0.2 and 0.6 for IP |
| Sotalol | 0.9% NaCl | S | Colorless | N | RT | 1 for IV |
| Haloperidol | 1% Tween 80/0.9% NaCl | I | White | N | RT | 6 for IP |

[a]This is based upon visual observation. S: soluble; I: insoluble (suspension or precipitation)
[b]Y: formula is kept in tube or vial with brown color, or covered with aluminum foil. N: no protection from light
[c]RT: prepared fresh and stored between 20-25° C.

2. Animals

Male Dunkin Hartley guinea pigs were obtained from National Laboratory Animal Center, Taiwan. Two guinea pigs were housed in each 47×23×21 cm animal cage. Animals were maintained in a controlled temperature (20-24° C.) and humidity (30%-70%) environment with 12-hour light/dark cycles for at least one week at laboratory of Eurofins Panlabs Taiwan, Ltd. prior to use. Free access to standard lab chow (PMI Nutrition International, Inc., USA) and sterile water in bottles was granted.

Male Wistar rats were provided by BioLasco Taiwan (under Charles River Laboratories Technology Licensee). Space allocation for 5 animals was 45×23×21 cm. Animals were housed in animal cages and maintained in a controlled temperature (20-24° C.) and humidity (30%-70%) environment with 12 hours light/dark cycles for at least three days in the laboratory of Eurofins Panlabs Taiwan, Ltd prior to use. Unless animals were fasted for special purpose, free access to standard lab chow for rats [MFG (Oriental Yeast Co., Ltd., Japan)] and sterile water was granted.

All aspects of this work including housing, experimentation and disposal of animals were performed in general accordance with the Guide for the Care and Use of Laboratory Animals (National Academy Press, Washington, D.C., 2011). Additionally, the study protocols were reviewed and approved by Eurofins Panlabs Taiwan, Ltd. IACUC.

3. Chemicals 0.9% NaCl (Sin-Tong, Taiwan), Haloperidol (Sigma, USA), Sotalol (Sigma, USA), Tween 80 (Sigma, USA) and Urethane (Sigma, USA).

4. Equipment

Animal cage (Allentown, USA), Beaker (1000 mL, Kimax, USA), Blood pressure transducer (P23XL, B. D., USA), Data acquisition and analytic system (Ponemah, DSI, USA), Disposal 1 mL syringe with needle (Terumo, Japan), ECG signal conditioner (20-4615-64, Gould, U. K.), Hypodermic needle 25G×1" (TOP Corporation, Japan), Rat scale (0-1000 g, Tanita, Japan), Rod (Suspended 10 cm above bench level), Stop watch (Casio, China), and Ventilator (683, Harvard, USA).

I. Result

Figure 5:
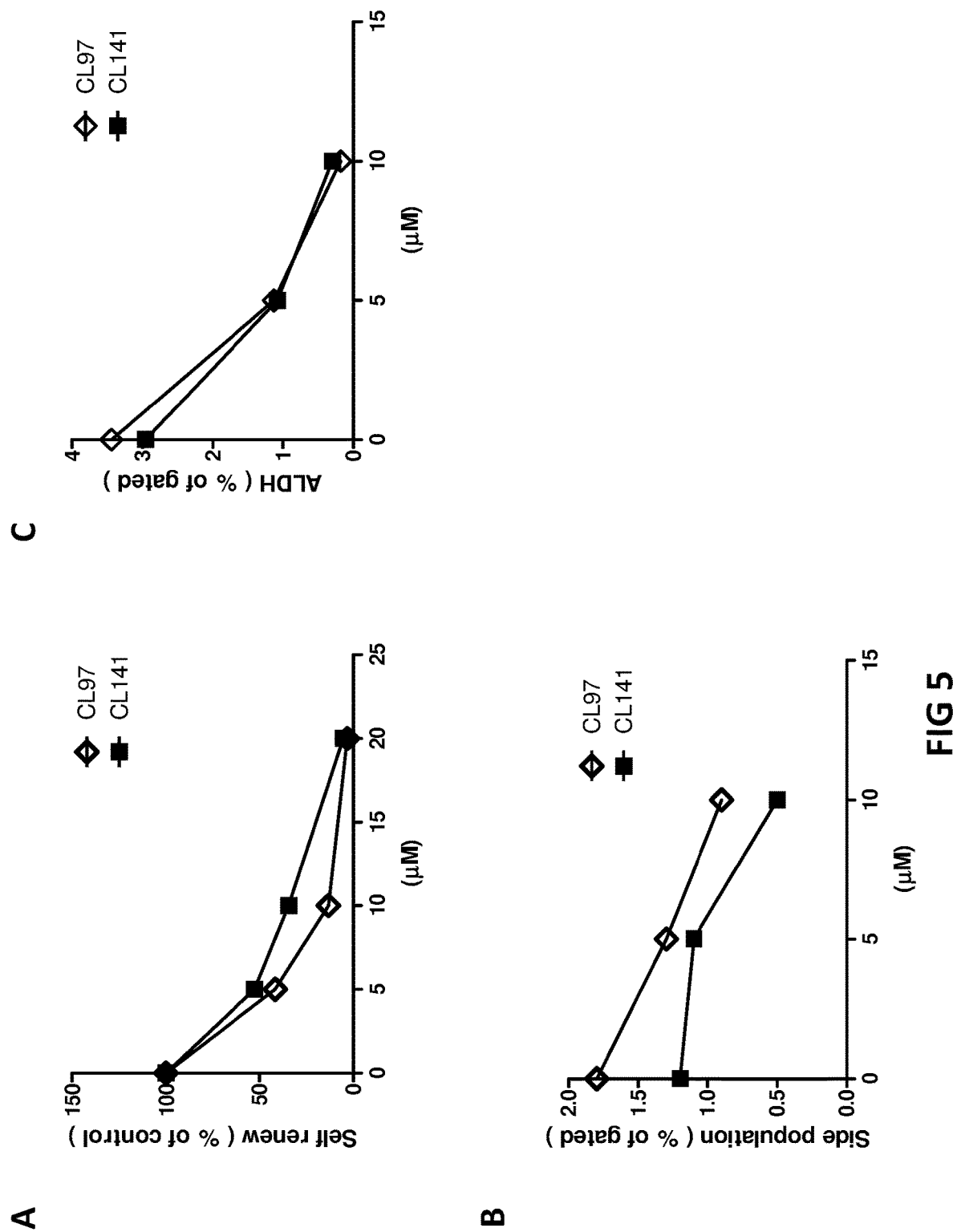
FIGS. 5A-C illustrate effectiveness of thioridazine in reducing percentage of non-small cell lung cancer stem-like cells.
Figure 6:
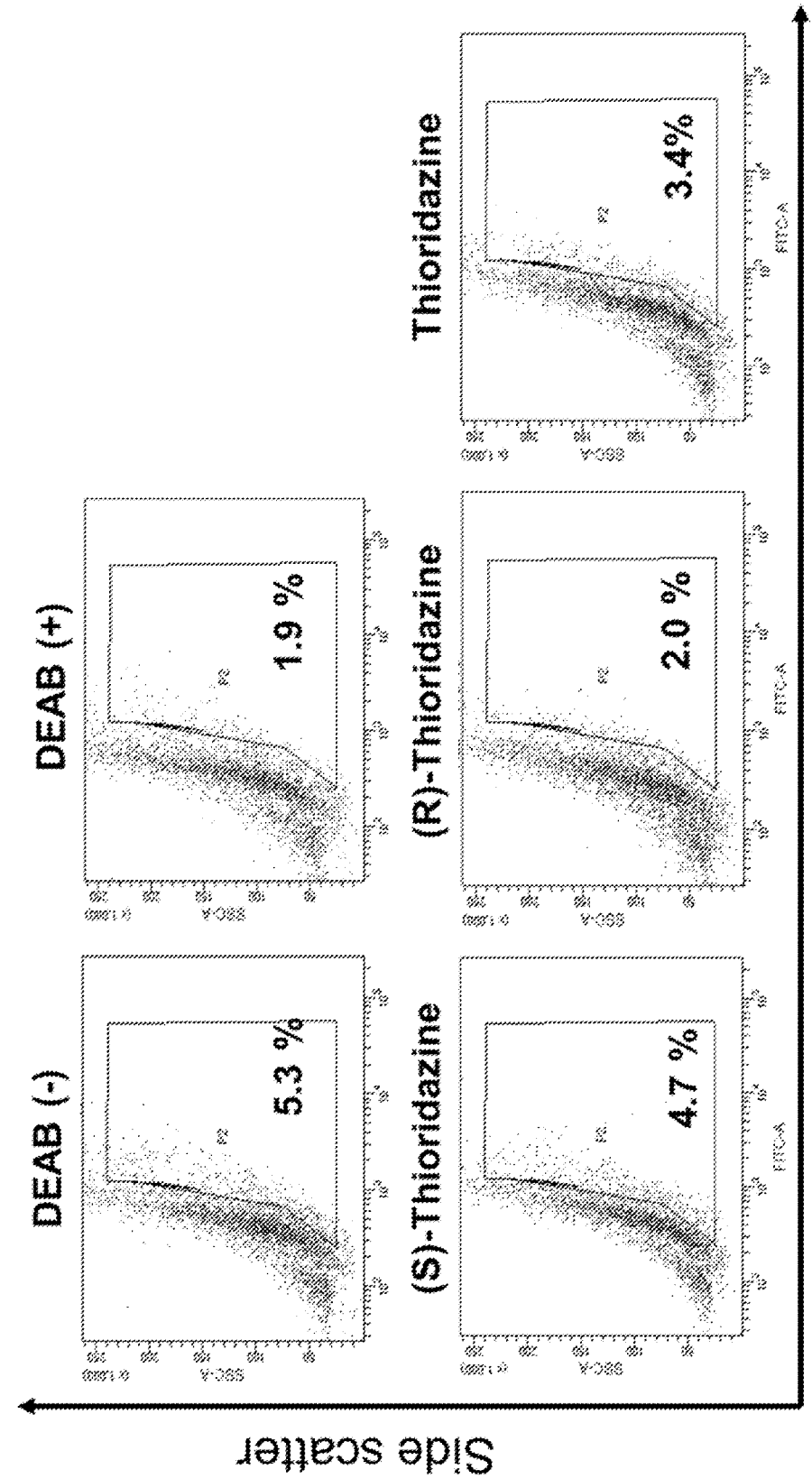
FIGS. 6 A-D illustrate ability of thioridazine and its enantiomers in inhibiting ALDH activity and sphere formation of A549 and CL141 cell lines.
Figure 6:
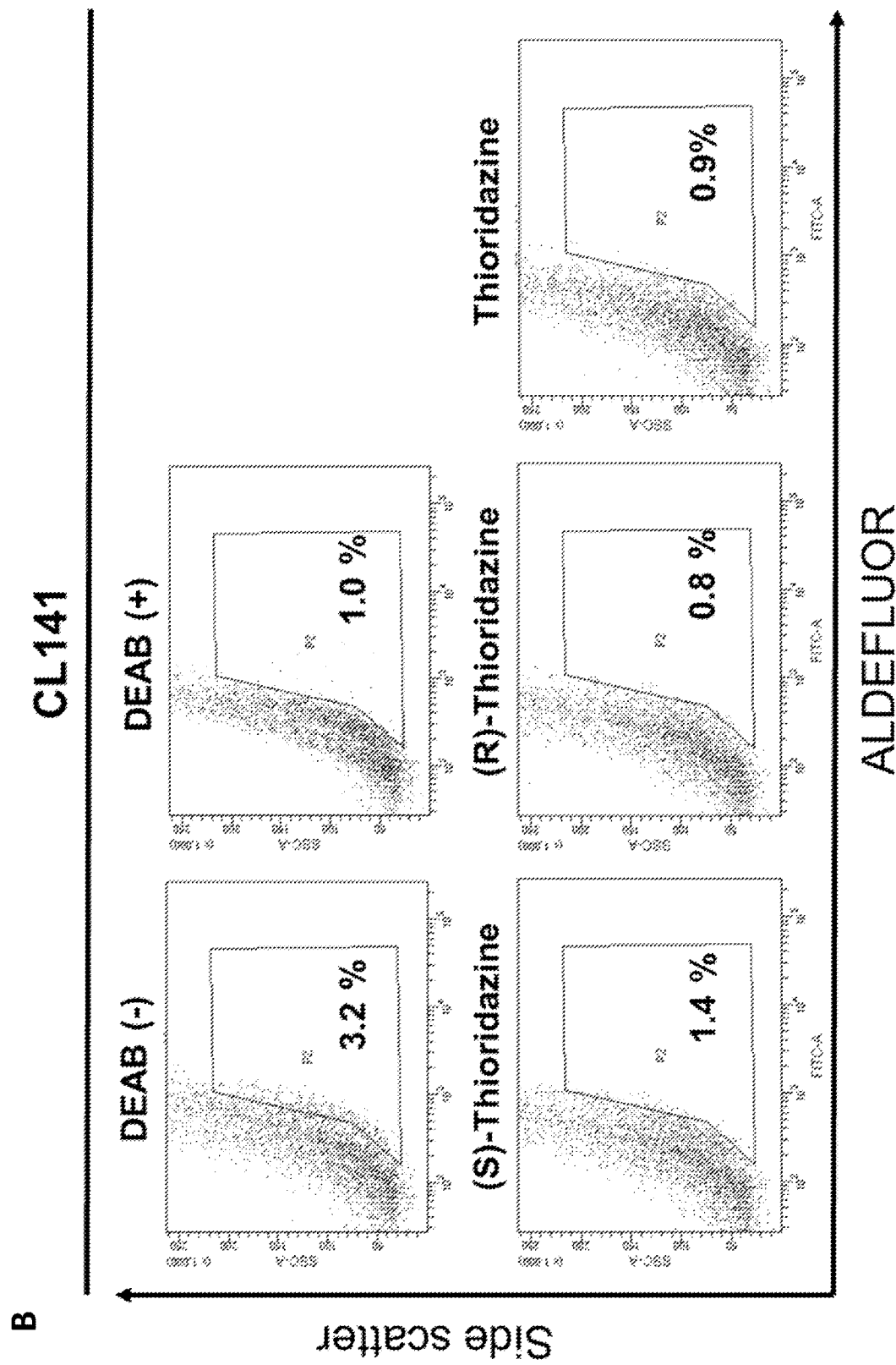
Figure 6:
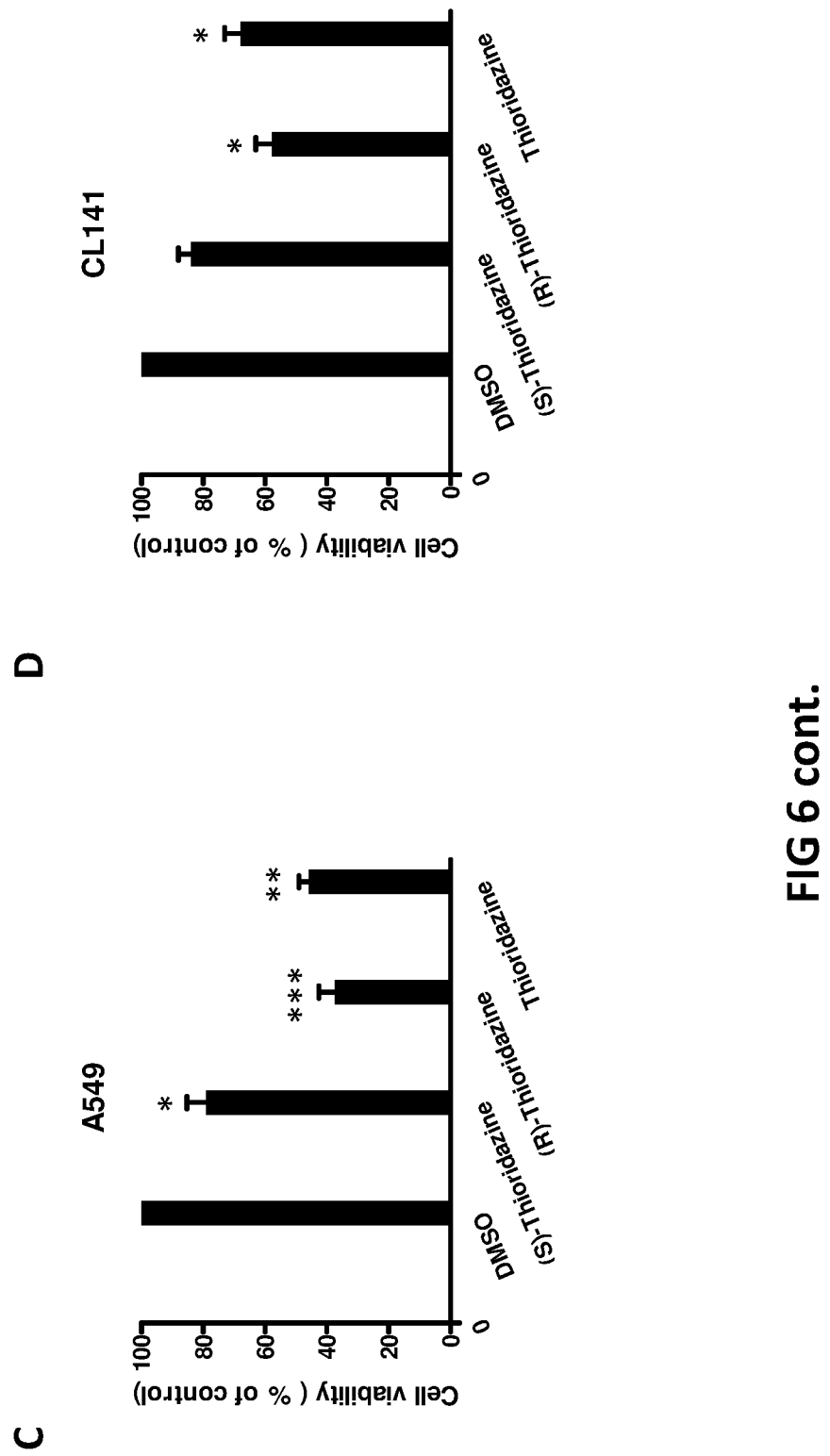

Thioridazine Significantly Inhibits the Self-Renewal of CL141 and CL97 Cancer Spheres Cancer stem cell (CSC) postulates the existence of a tumor cell population uniquely endowed with self-renewal capacity and therapy resistance[27]. Because thioridazine was predicted to preferentially inhibit lung CSC[24] using the Connectivity Map tool, we next examined whether the proportion of CL141 (a lung adenocarcinoma cell line expressing wild-type EGFR), CL97 (a lung adenocarcinoma cell line with EGFR exon 19 deletion and T790M mutations) CSC number could be diminished by thioridazine treatment. To test the inhibitory ability of thioridazine for self-renewal of CSC, we performed spheroid formation analysis in thioridazine-treated CL141 and CL97 CSCs. We found that the cell densities of spheroids decreased after 24 hrs in a dose-dependent manner after adding thioridazine (FIG. 5A).

Thioridazine Reduces the Proportion of Side Population Cells and ALDH$^+$ Cells in CL141 and CL97 Cell Lines To determine whether side population (SP) cells, which represent a cell population with CSC characteristics[28], exist in CL141 and CL97 human lung adenocarcinoma cancer cell lines, we stained the cells with Hoechst 33342, a fluorescent dye, and analyzed the cells using flow cytometry. After the exclusion of dead cells and cellular debris based on the scatter signals, we identified a small population of CL141 and CL97 cells with SP cell characteristics. After 48 hrs of incubation with thioridazine at 5 and 10 μM, the proportion of SP cells was dose dependently decreased (FIG. 5B). To further confirm our data, we investigated whether thioridazine treatment could reduce the percentage of the cells expressing ALDH, an established marker for both hematopoietic and NSCLC CSCs[29]. As shown in FIG. 5C, thioridazine treatment also decreased the ALDH$^+$ CL141 and CL97 cell populations in a dose-dependent manner Thioridazine and its Enantiomers Significantly Inhibit Sphere Formation in NSCLC Thioridazine enantiomers have been shown to have different targets and activity[26-30]. To further explore the role of thioridazine and its enantiomers, (S)- and (R)-thioridazine, we tested the CSC effect from two NSCLC cell lines (A549 and CL141). Thioridazine, (S)- and (R)-thioridazine suppressed the ALDH activity (FIGS. 6A-B) and spheroid-forming ability of the cells (FIGS. 6C-D). Interestingly, treatment with (S)-thioridazine seemed to result in lower sphere numbers and ALDH activity formed by these NSCLC cells than those of cells treated with (R)-thioridazine. Taken together, these data indicate that thioridazine exhibits a suppressive effect on NSCLC cancer cell self-renewal, as well as reduces the numbers of ALDH cells and side population cells.

The Activity of HMG-CoA Reductase is Inhibited by Thioridazine

Figure 7:
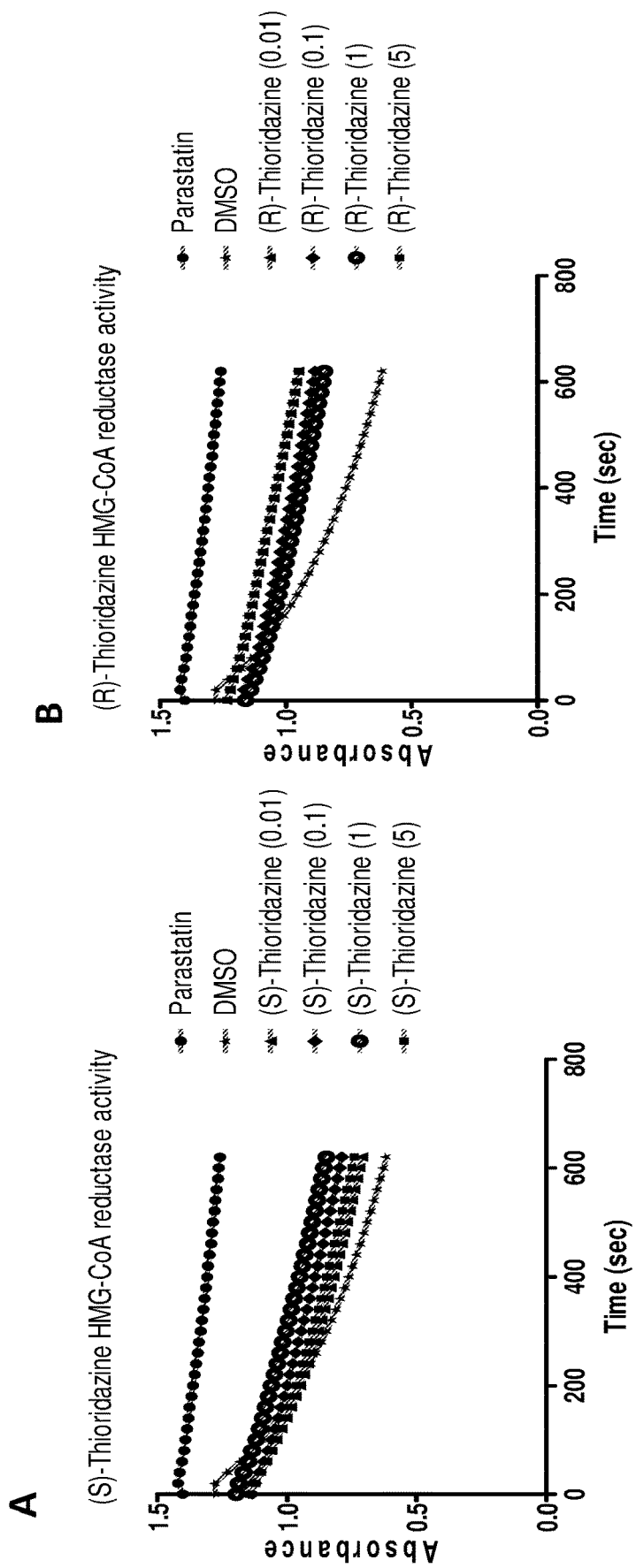
FIGS. 7A-D illustrate ability of thioridazine in inhibiting HMG-CoA reductase activity, where
Figure 7:
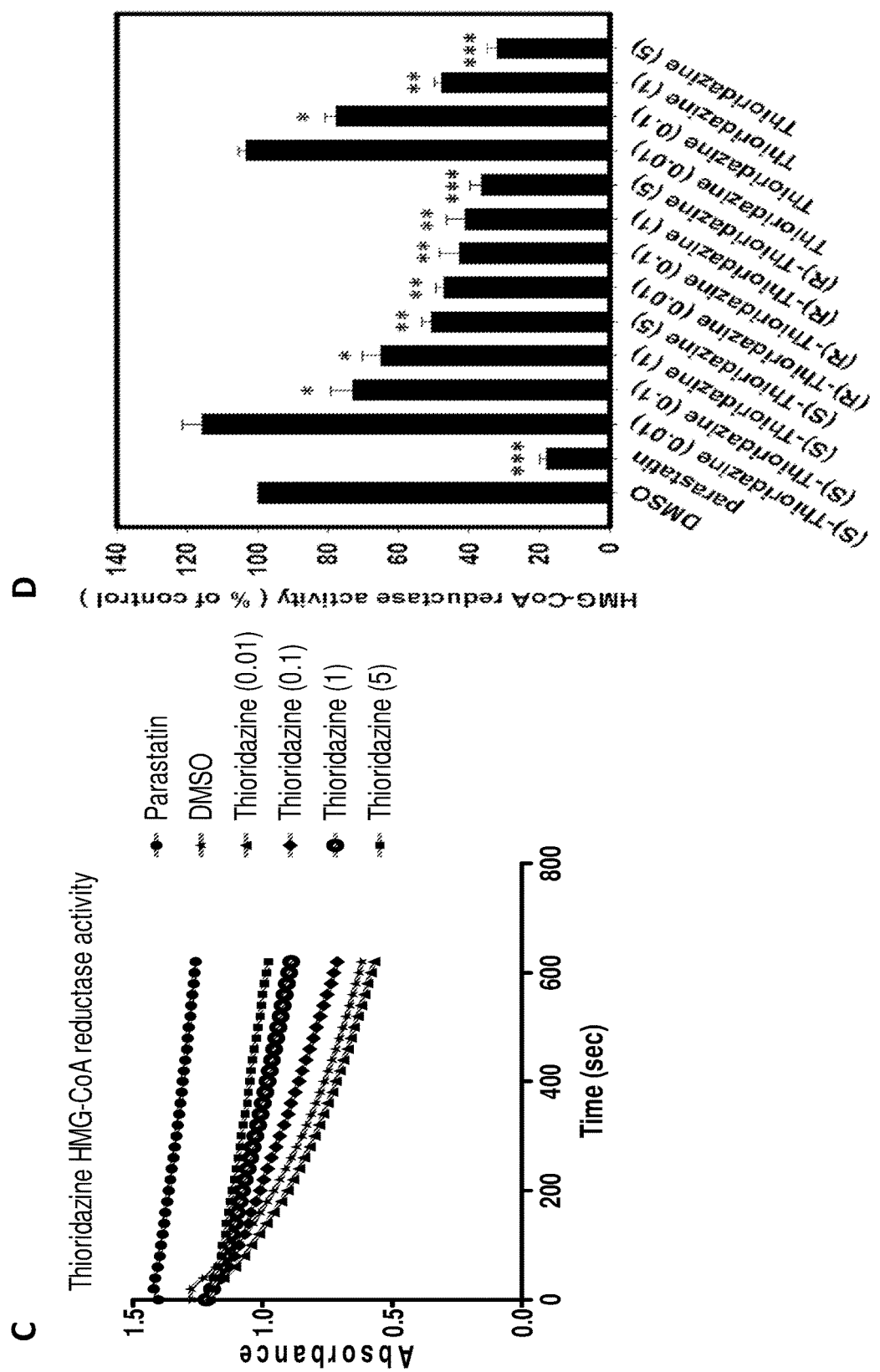

Cholesterol-lowering drugs, such as lovastatin, inhibit the growth of CSCs through the HMG-CoA reductase pathway[30]. Our bioinformatics analysis also predicted that thioridazine may affect cholesterol biosynthesis. We determined whether the activity of HMG-CoA reductase, the rate-limiting enzyme of cholesterol biosynthesis, was affected by thioridazine. The data showed that HMG-CoA reductase was inhibited by the single enantiomers and the racemic form of thioridazine to different degrees (FIGS. 7A-C). The activity of HMG-CoA reductase was inhibited more significantly by (S)-thioridazine at a lower concentration than by (R)-thioridazine. The racemic form of thioridazine had an inhibitory effect between that of (R)- and (S)-thioridazine (FIG. 7D).

Figure 8:
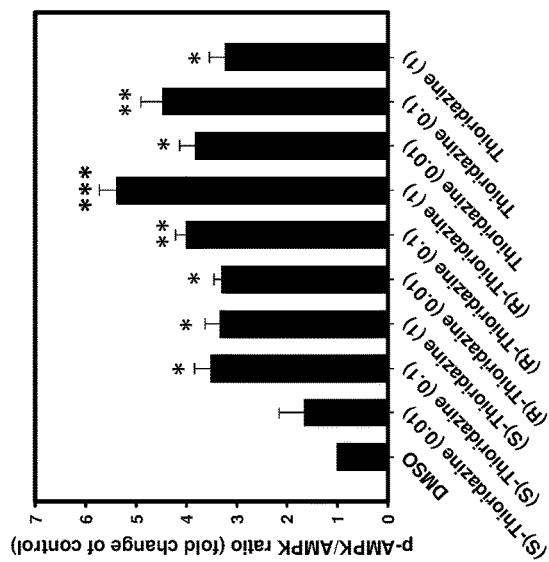
FIGS. 8A-B illustrate the ability of (S)-thioridazine, (R)-thioridazine and thioridazine in activating AMPK to affect cholesterol synthesis-related pathway at low concentration, where
Figure 8:
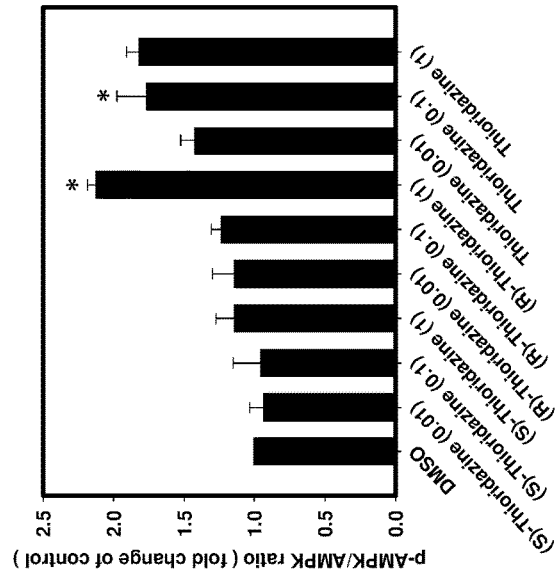
Figure 8:
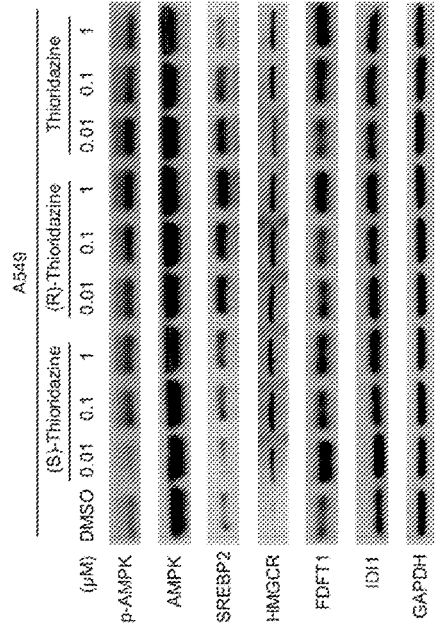
Figure 8:
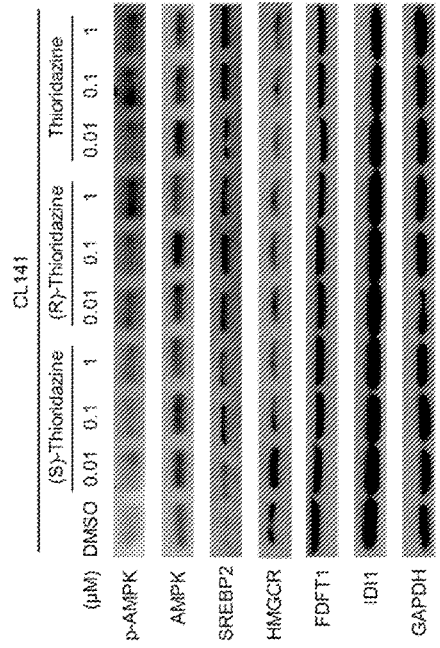

AMPK and the Cholesterol-Related Pathway are Induced by a Lower Concentration of Thioridazine Inhibition of cholesterol synthesis using HMG-CoA reductase inhibitor not only induces expression of SREBP2, but it also activates transcription of HMG-CoA reductase and other enzymes, which regulate the cholesterol synthesis pathways[31]. On the other hand, the short-term regulation of cholesterol biosynthesis depends on AMPK activation, which inhibits the activity of HMG-CoA reductase via phosphorylation. As a consequence, the relationship between the protein expression AMPK and that of cholesterol synthesis-related enzymes was determined. The Western blot data suggest that the cholesterol synthesis pathway rather than the geranylgeranyl pathway may be the most apparent regulator in the (S)-thioridazine-treated A549 and CL141 parental cells (FIG. 8). The activity of AMPK was activated at nM range in (S)-thioridazine-treated A549 parental cells. Interestingly, (S)-thioridazine is a better AMPK activator than (R)-thioridazine-treated cells.

Protein Expression of Stemness Marker and Cholesterol Synthesis-Related Enzymes is Reduced by Thioridazine in Lung Cancer Stem Cell Lines It has been reported that mRNA or protein levels of cholesterol synthesis-related enzymes were higher in breast CSCs compared with those in the parental cells[32]. High expression of several cholesterol synthesis-related enzymes was also observed in lung CSCs. In the present study, A549 and CL141 sphere cells and their corresponding parental cells were used to determine the expression level of cholesterol synthesis-related enzymes and CSC markers, such as CD133, Oct4, and Nanog. Western blot results showed that not only the stem cell marker but also the cholesterol synthesis-related enzymes were inhibited by the single enantiomer of thioridazine, (S)-thioridazine, at a concentration of 5 μM (FIGS. 9A-B).

Figure 10:
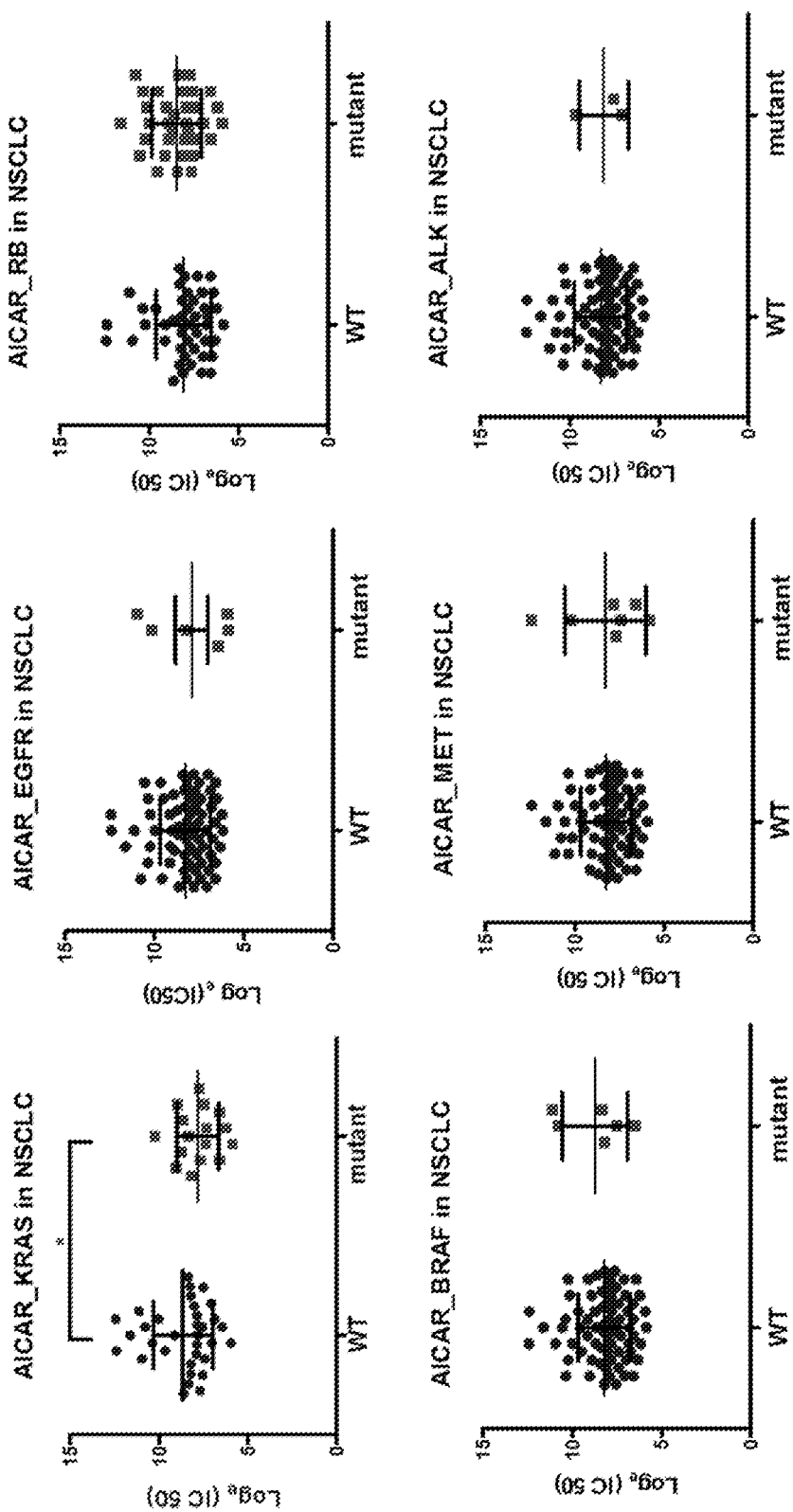
FIGS. 10 A-C illustrate that KRAS mutant cells are more sensitive to thioridazine than KRAS wild-type cells via the COSMIC and the colony formation analysis. Because thioridazine is a newly identified AMPK activator, we used the drug sensitivity data from another AMPK activator (AICAR) to infer that the KRAS mutant cells might be more sensitive to thioridazine than KRAS wild-type cells.
Figure 10:
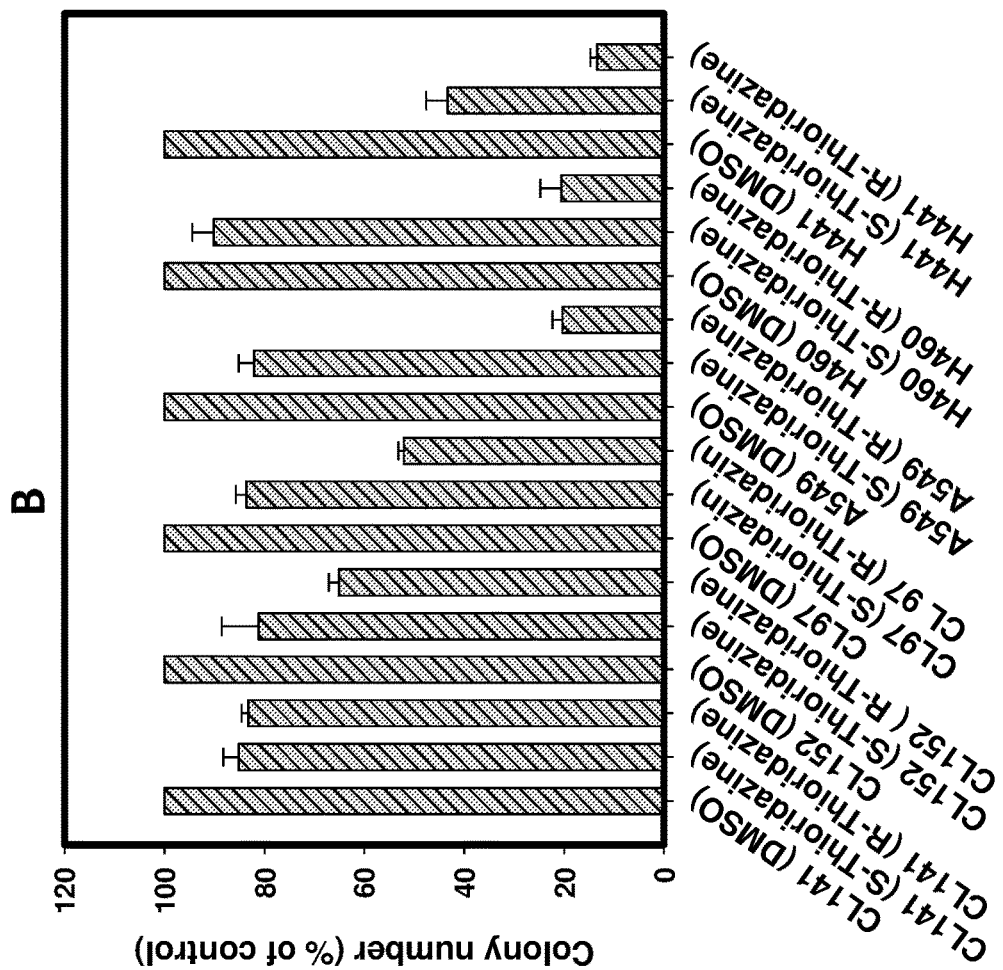
Figure 10:
Figure 11:
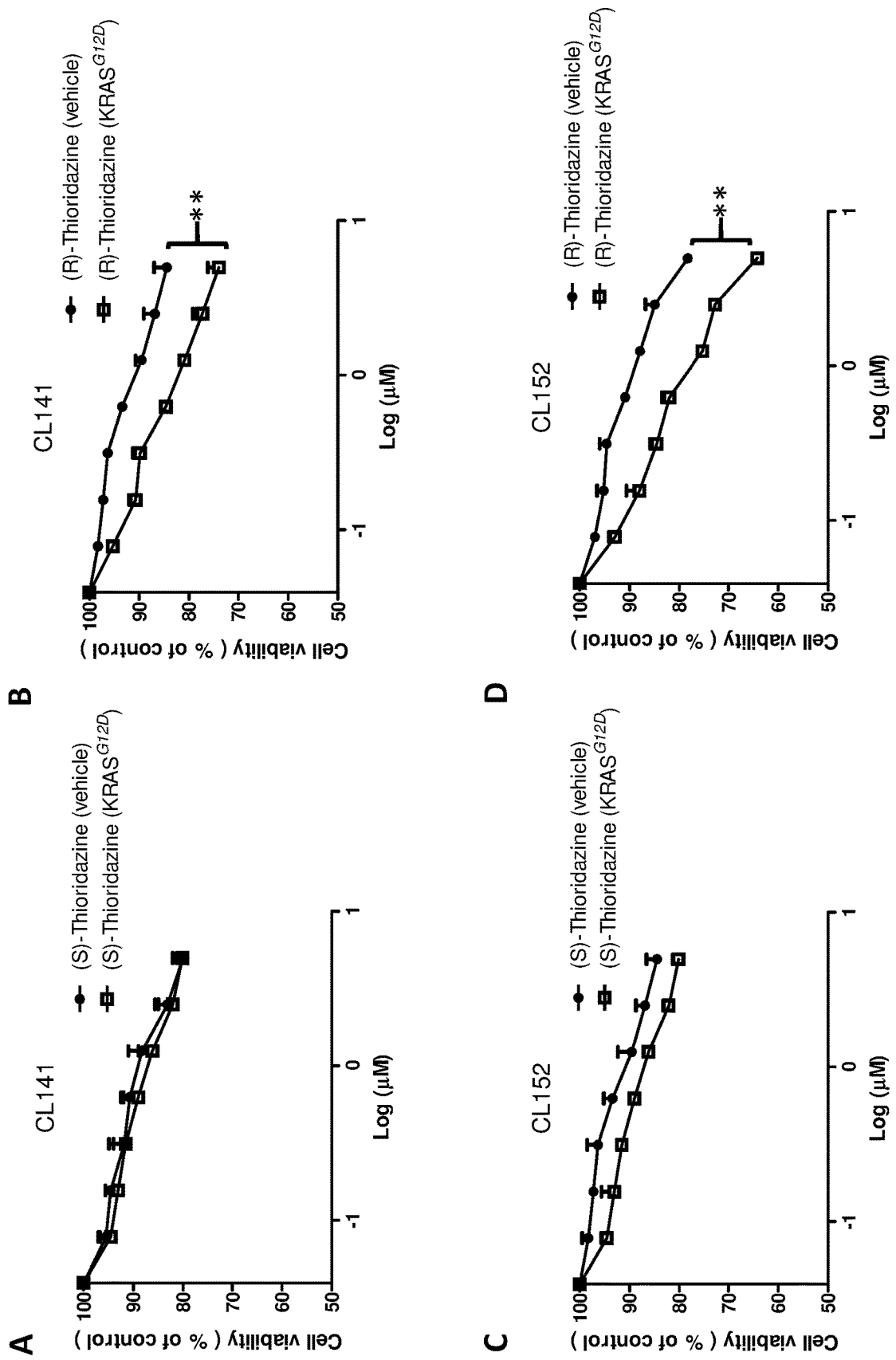
FIGS. 11A-D illustrate that KRAS wild-type cells are sensitized to thioridazine through $KRAS^{G12D}$ transfection. After the $KRAS^{G12D}$ transfection, CL141 and CL152 cells were further treated with thioridazine from 0.1 µM to 5 µM for 48 hrs, and cell viability was determined via SRB assay.

The COSMIC and the Colony Formation Analysis Suggest that the KRAS Mutant Cells are More Sensitive to Thioridazine To search for a genetic marker to guide further clinical trial, we employed the characteristics of thioridazine as an AMPK activator to guide our bioinformatics analysis. Using the data stored at the COSMIC (http://cancer.sanger.ac.uk/cosmic), we found that the KRAS mutation cells appear to be more sensitive to the AMPK activator (AICAR) than the KRAS wild-type cells; whereas there was no significant difference in sensitivity to the AMPK activator between the other mutations frequently observed in the NSCLC and wild-type cells (FIG. 10A). Since 30% of somatic NSCLCs harbor LKB1 inactivating mutations and are often associated with KRAS mutations, cells with KRAS mutations may be more sensitive to AMPK activators. Therefore, we hypothesized that thioridazine might exhibit similar characteristics to AICAR since both compounds are AMPK activators. In concordance with the COSMIC analysis, there was differential sensitivity to thioridazine between the KRAS mutant cells and the KRAS wild-type cells. Clonogenicity of the KRAS wild-type (CL14, CL152, and CL97) and mutant cell lines (A549, H460, and H441) was reduced after exposure to 5 μM thioridazine and its enantiomers, respectively (FIGS. 10B-C). Of particular interest was that (S)-thioridazine more effectively inhibited the colony formation in the KRAS mutant cell lines than (R)-thioridazine.

The KRAS Wild-Type Cells are Sensitized to Thioridazine Through $KRAS^{G12D}$ Transfection Pancreatic cells that have a KRAS mutation and that require de novo fatty acid (FA) synthesis for lipids ('lipogenic cells') were unable to synthesize FA from acetyl-CoA in the presence of inhibitors of cholesterol synthesis, including statins. Moreover, KRAS mutant lung cancer cells were also observed to have higher sensitivity to thioridazine than KRAS wild-type cells (FIG. 11B); thus, it is reasonable to hypothesize that the KRAS mutation may result in metabolic reprogramming of the cancer cells and alter their sensitivity to thioridazine. As a consequence, the CL141 and CL152 (KRAS wild-type cells) were transfected with the $KRAS^{G12D}$ plasmid to test the sensitivity to thioridazine. The results demonstrated that both KRAS wild-type cell lines (CL141 and CL152) were sensitized to (S)-thioridazine but not to (R)-thioridazine after $KRAS^{G12D}$ transfection (FIGS. 11A-D).

Thioridazine Inhibits the Viability of A549 Through AMPK Activation

As shown previously, AMPK was upstream of cholesterol biosynthesis and was activated by thioridazine in the nM range. To investigate whether the viability of KRAS mutant cells was inhibited by thioridazine through AMPK activation, A549 cells were transfected with dominant negative AMPK for 16 ~24 hrs and further treated with thioridazine from 0.1 to 5 μM for 48 hrs. The viability of A549 (KRAS mutant cells) was recovered when the cells were transfected with the dominant negative AMPK compared with the parental cells in the (S)-thioridazine treatment groups (FIG. 12D). However, there was no significant difference between the dominant negative AMPK-transfected cells and the parental cells in the (R)-thioridazine treatment groups (FIG. 12C).

Figure 13:
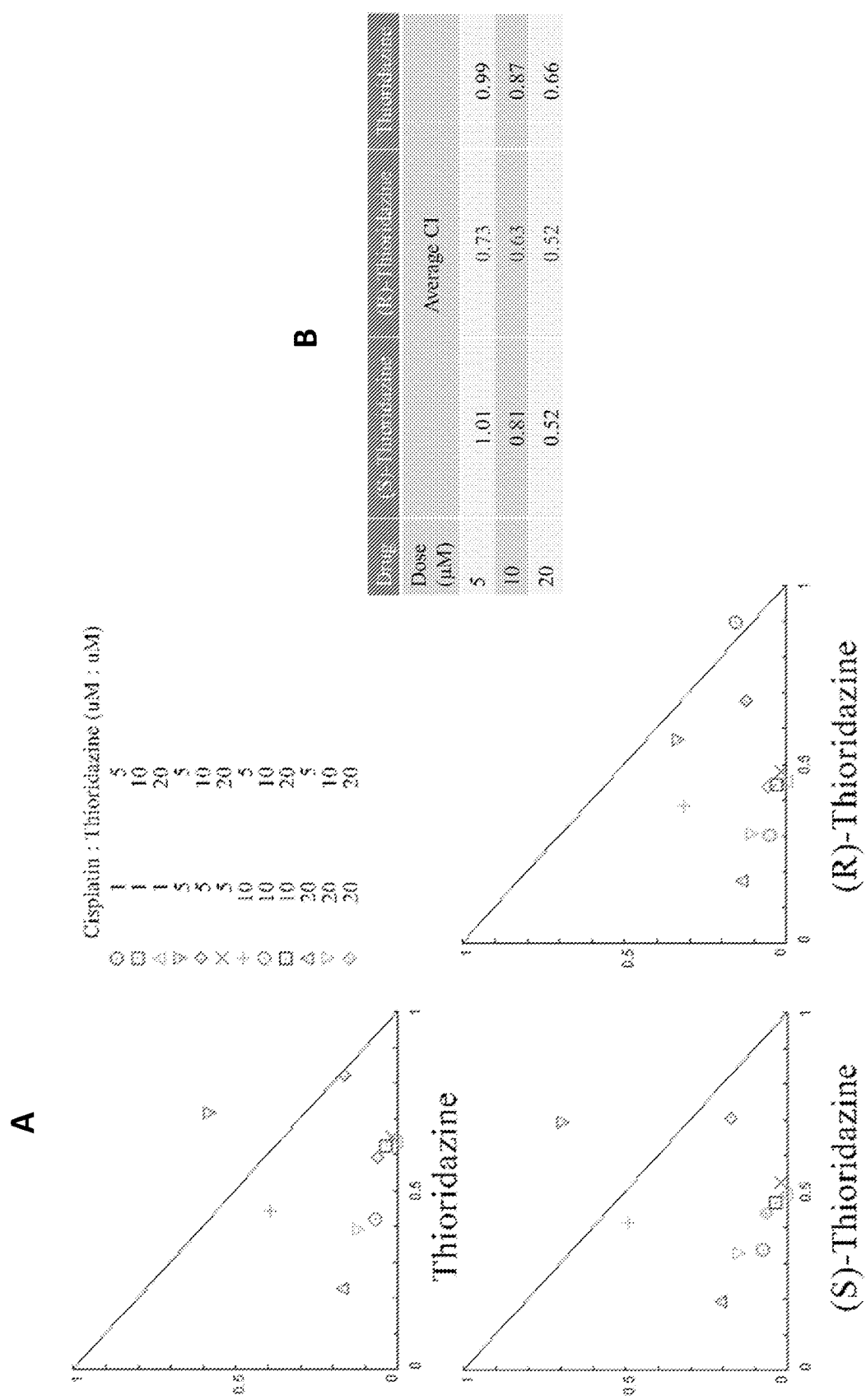
FIGS. 13A-B illustrate results of synergy analysis of each of thioridazine and its enantiomers combined with cisplatin in the CL152 cells. CL152 cells were exposed to thioridazine or its enantiomers combined with cisplatin simultaneously for 72 hrs. Isobologram, illustrated in FIG. 13A, and combination index (CI) methods, illustrated in FIG. 13B, were used to analyze and confirm synergistic combination of cisplatin with thioridazine or its enantiomers. The average CI values were calculated from each individual dose (5, 10 or 20 μM) of thioridazine and its enantiomers. The values of the CIs are: CI>1, antagonism; CI=1, additivity; CI<1, synergism. The lowest CI value indicates the best synergistic effect of the combination of two drugs for inhibition of cell viability.

Thioridazine Synergistically Enhances Cytotoxicity in Combination with Cisplatin or Gemcitabine in NSCLC Cells Cisplatin and gemcitabine are chemotherapeutic agents frequently used for the treatment of NSCLC. The combined effect of thioridazine with cisplatin or gemcitabine was investigated by a SRB assay and analyzed by Isobologram analysis (CompuSyn software). We first tested the synergistic effect of thioridazine and its enantiomers combined with cisplatin in CL152 cells (squamous cell carcinoma). As shown in FIGS. 13A and 13B, thioridazine and its enantiomers had a synergistic effect in combination with cisplatin. Furthermore, thioridazine or its enantiomers plus gemcitabine showed similar synergistic effects in A549 (adenocarcinoma with EGFR-wild type), H2170 (squamous cell carcinoma) and H1299 (large cell carcinoma), and CL97 (adenocarcinoma cell harboring EGFR-T790M mutation) cell lines after 48 hrs of treatment (FIG. 17). Interestingly, (S)-thioridazine, particularly at low dosages (5 or 10 μM), had lower CI values in combination with cisplatin, indicating that (S)-thioridazine may have a better therapeutic effect in combination with cisplatin than thioridazine and (R)-thioridazine in NSCLC.

Figure 14:
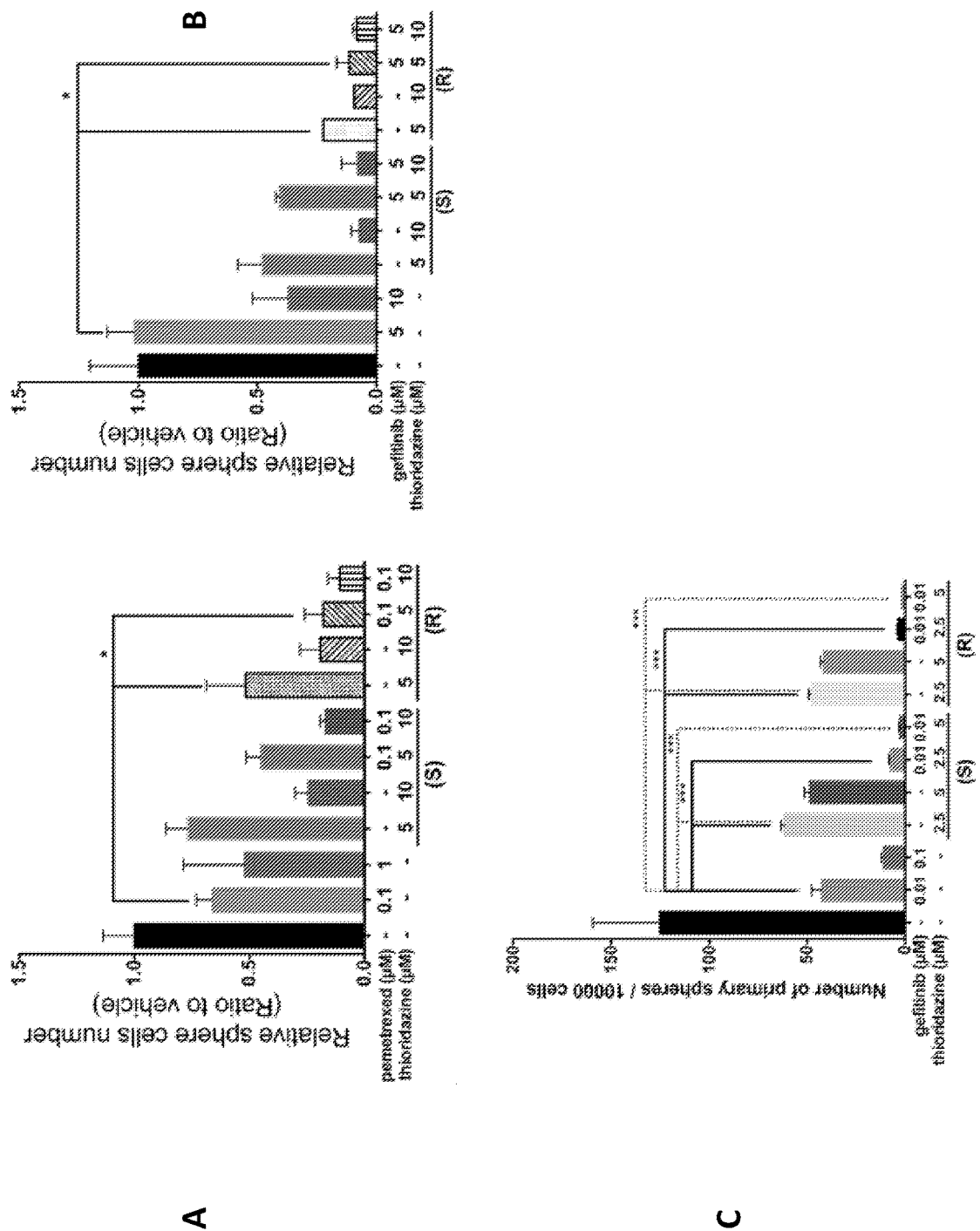
FIGS. 14A-C illustrate results of synergistic analysis of the (S)- and (R)-thioridazine combined with anti-cancer drugs in NSCLC sphere cells. CL141 secondary sphere cells and CL97 secondary sphere cells were dissociated and seeded 10000 cells/well in 24-well ultralow attachment plates and then treated with (S)- and (R)-thioridazine alone, pemetrexed (CL141 cells) or gefitinib (CL97 cells) alone, or in combination with (S)- or (R)-thioridazine plus pemetrexed or gefitinib for 48 hrs, as indicated. Spheres were dissociated and counted using the Trypan Blue Exclusion method. The results are shown in FIG. 14A for CL141 cells and FIG. 14B for CL97 cells. For primary sphere-forming assay, HCC827 cells were dissociated and seeded 10000 cells/well in 24-well ultralow attachment plates in DMEM/F12 medium content N2 supplement, EGF (20 ng/ml) and bFGF (20 ng/ml). After 4 days, cells treated with (S)-thioridazine, (R)-thioridazine and gefitinib alone or in combination with (S)- or (R)-thioridazine plus gefitinib for 48 hrs. Spheres number (>80 μm) were observed and measured by a microscope. * $P<0.05$,  $P<0.01$, * $P<0.001$. The results are shown in FIG. 14C.

(S)- and (R)-Thioridazine Significant Inhibits the Self-Renewal of NSCLC Cancer Spheres To evaluate whether the thioridazine alone or combined with chemotherapeutic agents or EGFR-TKI gefitinib could suppress NSCLC cancer stem-like sphere cells in vitro, NSCLC cell lines, including CL141, CL152 and HCC827 cells, were plated in stem cell conditioned culture system allowed for sphere forming. CL141 and CL97 secondary sphere cells were treated with (S)- and (R)-thioridazine alone, pemetrexed (CL141 cells) or gefitinib (CL97 cells) alone, or a combined treatment for 48 hrs. As shown in FIGS. 14A and 14B, (S)- and (R)-thioridazine suppress CL141 and CL97 secondary sphere cells viability (FIGS. 14A and B). The combination, co-treatment with (S)-thioridazine (5 μM) and clinical drugs, also significantly decreased the number of sphere cells compared to (S)-thioridazine, pemetrexed or gefitinib alone (FIGS. 14A and B). In addition, (S)- and (R)-thioridazine also suppressed the primary sphere-forming ability from HCC827 cells (FIG. 14C). Interestingly, (S)-thioridazine in combination with gefitinib seemed to have lower sphere number than that of cells treated with (S)- and (R)-thioridazine or gefitinib alone. Taken together, these data suggest that both (S)- and (R)-thioridazine have anti-CSC ability on these tested sphere cells and combination of (S)- or (R)-thioridazine with chemotherapeutic agents or EGFR-TKI may have benefited to cancer therapy. It should note that the data also indicate that (S)-thioridazine may have better therapeutic benefits on anti-CSCs in NSCLC compared with (R)-thioridazine.

In Vivo Examination of Tumor Inhibitory Effects of Thioridazine and its Enantiomers in Combination with Pemetrexed The anti-lung cancer effects of thioridazine and its enantiomers, and an anti-psychotic drug, trifluoperazine (TFP), were evaluated in H441-bearing mice. TFP was used as a reference control for comparison with the previous data[24]. Four weeks post treatment, it was clear that all three thioridazine tested and TFP (at 5 mg/kg) were effective in suppressing tumor growth compared with the vehicle controls as demonstrated by both bioluminescence images (FIG. 15A) and semi-quantitative analysis (FIG. 15B). Because the tumor suppressive effects of all drug-treated groups were significantly higher than those of the control group, the control group was removed to differentiate and compare the efficacy of different drugs. However, at 5 mg/kg, all drugs exhibited a similar degree of tumor suppressive effects (from our semi-quantitative analysis), and there was no significant difference observed between the drug-treated groups. Subsequently, we reduced the dosage of thioridazine to 3 mg/kg to differentiate the tumor suppressive effects among the drugs could be distinguished at a lower concentration. According to our results, at 3 mg/kg, (S)-thioridazine exhibited the most significant tumor suppressive effects as compared to those of (R)-thioridazine and thioridazine (FIG. 15C). This observation was in agreement with our in vitro data where (S)-thioridazine exhibited a superior better anti-lung cancer stem cell activity (e.g., sphere formation assay in FIG. 6) than thioridazine and (R)-thioridazine.

Next, we examined the feasibility of using thioridazine and its enantiomers (1 mg/kg) in combination with pemetrexed (1 mg/kg) (a standard chemotherapeutic agent for NSCLC) in H441-bearing NOD/SCID mice. We found that thioridazine and (R)-thioridazine (both at 1 mg/kg) in combination with pemetrexed did not differ from pemetrexed alone (1 mg/kg) in terms of tumor suppressive effects (FIG. 15D). However, the tumor suppressive effects of combined treatment with (S)-thioridazine and pemetrexed appeared to be the most significant (FIG. 15D). Taken together, (S)-thioridazine may have therapeutic anti-CSC benefits, either alone or in combination with other agents, represents a superior anti-lung CSC agent than (R)-thioridazine and thioridazine. Finally, western blot analysis of the tissue biopsy demonstrated that the AMPK was activated after the (S)-thioridazine treatment (FIG. 15E). The downstream signaling of AMPK, FDFT1, was also inhibited in (S)-thioridazine treatment group. N=2 (mice samples) in each treatment group, *** P<0.001.

Figure 9:
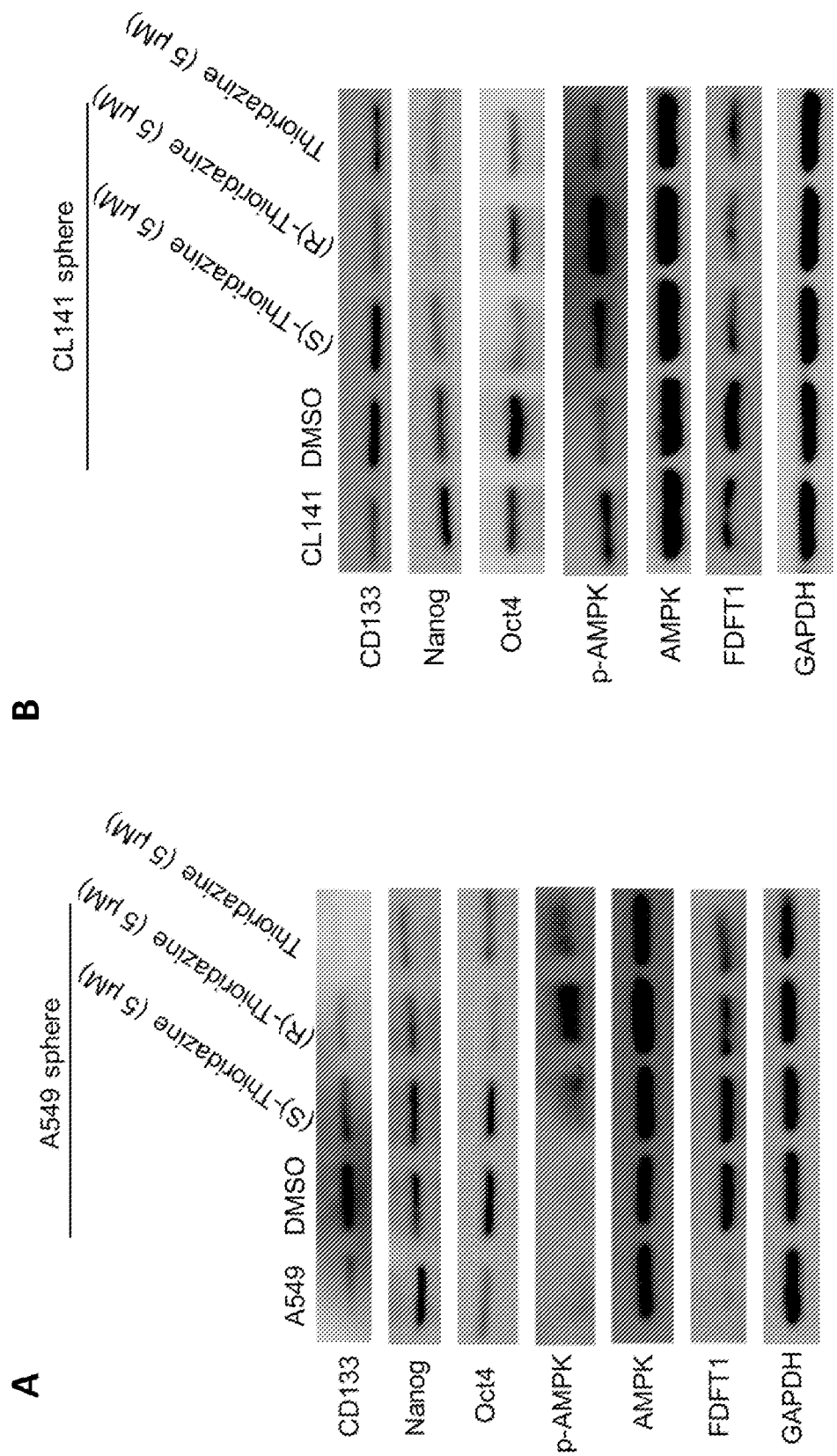
FIGS. 9A-B illustrate the ability of thioridazine in inhibiting the stemness markers and cholesterol synthesis-related enzymes through the mevalonate pathway in lung cancer stem cells, where

In summary, the RNA expression of the cholesterol biosynthesis enzymes was significantly up-regulated in lung CSCs compared with parental cells (FIG. 9). A similar phenomenon was observed in the breast CSCs, particularly in mesenchymal tumor spheres. In addition, mutant KRAS may initiate tumorigenesis by expanding a susceptible stem/progenitor cell population, and the KRAS mutant cells may have higher expression of some stemness markers, including CD133, Oct4, and Nanog. Our data revealed that the cholesterol biosynthesis enzymes were up-regulated in the KRAS mutant cells and the KRAS wild-type spheres compared with the parental cells, while the stemness and the sphere viability results suggested that the KRAS mutant cells were more dependent on cholesterol biosynthesis than KRAS wild-type cells. The $KRAS^{G12D}$ transfection data demonstrated that KRAS wild-type cells are more sensitive to (S)-thioridazine after transfection with $KRAS^{G12D}$. These data raised the possibility that the KRAS mutation may shunt the metabolism of KRAS wild-type cells toward cholesterol biosynthesis and further lead to the increased sensitivity to (S)-thioridazine. Although the relationship between KRAS mutations and the reprogramming of the cholesterol biosynthesis in lung cancer should be further investigated in the future, the KRAS mutation could be exploited for patient selection in clinical trials.

(S)-Thioridazine Enantiomer Substantially Less Likely to Cause Catalepsy

Test compounds were administered at escalating doses (0.3, 1 and 3 mg/kg) by intraperitoneal injection to the same 5 Wistar-derived male rats weighing 130±20 g and observed over a 30 minute period for induction of catalepsy (potential adverse extra-pyramidal activity). The next dose was given after a 3-days washout. Catalepsy was evaluated by placing rat forepaws on a rod suspended 10 cm above bench level and scored positive if this abnormal posture is maintained for more than 5 seconds. Activity is considered significant when observed in 3 or more (>=3) of 5 animals. As can be seen in results summarized in FIG. 16 that (S)-thioridazine is the only one out of the three forms of thioridazine tested that did not cause catalepsy.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

REFERENCES

1. Siegel, R., Naishadham, D. & Jemal, A. Cancer statistics, 2012. CA Cancer J Clin 62, 10-29 (2012).
2. Pfister, D. G., et al. American Society of Clinical Oncology treatment of unresectable non-small-cell lung cancer guideline: update 2003. J Clin Oncol 22, 330-353 (2004).
3. Gronberg, B. H., et al. Phase III study by the Norwegian lung cancer study group: pemetrexed plus carboplatin compared with gemcitabine plus carboplatin as first-line chemotherapy in advanced non-small-cell lung cancer. J Clin Oncol 27, 3217-3224 (2009).
4. Sadowska, A. M., et al. Customizing systemic therapy in patients with advanced non-small cell lung cancer. Ther Adv Med Oncol 3, 207-218 (2011).
5. Stinchcombe, T. E. & Socinski, M. A. Current treatments for advanced stage non-small cell lung cancer. Proc Am Thorac Soc 6, 233-241 (2009).
6. Glare, P. Clinical predictors of survival in advanced cancer. J Support Oncol 3, 331-339 (2005).
7. Bao, S., et al. Glioma stem cells promote radioresistance by preferential activation of the DNA damage response. Nature 444, 756-760 (2006).
8. Clevers, H. The cancer stem cell: premises, promises and challenges. Nat Med 17, 313-319 (2011).
9. Diehn, M., et al. Association of reactive oxygen species levels and radioresistance in cancer stem cells. Nature 458, 780-783 (2009).
10. Gupta, P. B., et al. Identification of selective inhibitors of cancer stem cells by high-throughput screening. Cell 138, 645-659 (2009).
11. Eramo, A., et al. Identification and expansion of the tumorigenic lung cancer stem cell population. Cell Death Differ 15, 504-514 (2008).
12. Leung, E. L., et al. Non-small cell lung cancer cells expressing CD44 are enriched for stem cell-like properties. PLoS One 5, e14062 (2010).
13. Pirozzi, G., et al. Epithelial to mesenchymal transition by TGFbeta-1 induction increases stemness characteristics in primary non small cell lung cancer cell line. PLoS One 6, e21548 (2011).
14. Storms, R. W., Goodell, M. A., Fisher, A., Mulligan, R. C. & Smith, C. Hoechst dye efflux reveals a novel CD7(+) CD34(−) lymphoid progenitor in human umbilical cord blood. Blood 96, 2125-2133 (2000).
15. Ginestier, C., et al. ALDH1 is a marker of normal and malignant human mammary stem cells and a predictor of poor clinical outcome. Cell Stem Cell 1, 555-567 (2007).
16. Chou, F. H., Tsai, K. Y., Su, C. Y. & Lee, C. C. The incidence and relative risk factors for developing cancer among patients with schizophrenia: a nine-year follow-up study. Schizophr Res 129, 97-103 (2011).

17. Chen, Q. Y., et al. Molecular mechanism of trifluoperazine induces apoptosis in human A549 lung adenocarcinoma cell lines. Mol Med Rep 2, 811-817 (2009).
18. Tzadok, S., et al. In vitro novel combinations of psychotropics and anti-cancer modalities in U87 human glioblastoma cells. Int J Oncol 37, 1043-1051 (2010).
19. Sachlos, E., et al. Identification of drugs including a dopamine receptor antagonist that selectively target cancer stem cells. Cell 149, 1284-1297 (2012).
20. Kang, S., et al. Thioridazine induces apoptosis by targeting the PI3K/Akt/mTOR pathway in cervical and endometrial cancer cells. Apoptosis 17, 989-997 (2012).
21. Rho, S. B., Kim, B. R. & Kang, S. A gene signature-based approach identifies thioridazine as an inhibitor of phosphatidylinositol-3'-kinase (PI3K)/AKT pathway in ovarian cancer cells. Gynecol Oncol 120, 121-127 (2011).
22. Strobl, J. S., et al. Inhibition of human breast cancer cell proliferation in tissue culture by the neuroleptic agents pimozide and thioridazine. Cancer Res 50, 5399-5405 (1990).
23. Pantazaki, A. A. & Lialiaris, T. S. A combined biochemical and cytogenetic study of thioridazine-induced damage to nucleic acids. Mutagenesis 14, 243-248 (1999).
24. Yeh, C. T., et al. Trifluoperazine, an antipsychotic agent, inhibits cancer stem cell growth and overcomes drug resistance of lung cancer. Am J Respir Crit Care Med 186, 1180-1188 (2012).
25. Thanacoody, H. K. Thioridazine: resurrection as an antimicrobial agent? Br J Clin Pharmaco 164, 566-574 (2007).
26. Svendsen, C. N., et al. Receptor affinity, neurochemistry and behavioral characteristics of the enantiomers of thioridazine: evidence for different stereoselectivities at D1 and D2 receptors in rat brain. Neuropharmacology 27, 1117-1124 (1988).
27. Sourisseau, T., et al. Lung cancer stem cell: fancy conceptual model of tumor biology or cornerstone of a forthcoming therapeutic breakthrough? J Thorac Oncol 9, 7-17 (2014).
28. Ho, M. M., Ng, A. V., Lam, S. & Hung, J. Y. Side population in human lung cancer cell lines and tumors is enriched with stem-like cancer cells. Cancer Res 67, 4827-4833 (2007).
29. Sullivan, J. P., et al. Aldehyde dehydrogenase activity selects for lung adenocarcinoma stem cells dependent on notch signaling. Cancer Res 70, 9937-9948 (2010).
30. Kimberly A Hartwell, et al. Niche-based screening identifies small-molecule inhibitors of leukemia stem cells. Nat Chem Biol 9, 840-848 (2013).
31. Fraser J. Sim., et al. Statin treatment of adult human glial progenitors induces PPARy-mediated oligodendrocytic differentiation. GLIA 56, 954-962 (2008)
32. Christophe Ginestier, et al. Mevalonate Metabolism Regulates Basal Breast Cancer Stem Cells and Is a Potential Therapeutic Target. STEM CELLS 30, 1327-1337 (2012)

We claim:

1. A method for treating human non-small-cell lung cancer (NSCLC) in a subject, comprising administering to the subject in need thereof a therapeutically effective amount of a pharmaceutical composition comprising (S)-thioridazine or a pharmaceutically acceptable salt thereof, and a pharmaceutically acceptable carrier wherein the pharmaceutical composition is free of (R)-thioridazine.

2. A method for treating human NSCLC in a subject, comprising administering to the subject in need thereof a therapeutically effective amount of a pharmaceutical composition comprising (S)-thioridazine or a pharmaceutically acceptable salt thereof, and a pharmaceutically acceptable carrier wherein the pharmaceutical composition is substantially free of (R)-thioridazine.

3. A method for treating human NSCLC in a subject by inhibiting cholesterol synthesis enzymes in cancer stem cells (CSCs), comprising the step of administering to the subject a therapeutically effective amount of a pharmaceutical composition comprising (S)-thioridazine or a pharmaceutically acceptable salt thereof, and a pharmaceutically acceptable carrier wherein the pharmaceutical composition is free of (R)-thioridazine.

4. A method for treating human NSCLC in a subject by activating AMPK in CSCs, comprising the step of administering to the subject a therapeutically effective amount of a pharmaceutical composition comprising (S)-thioridazine or a pharmaceutically acceptable salt thereof, and a pharmaceutically acceptable carrier wherein the pharmaceutical composition is free of (R)-thioridazine.

5. The method of claim 1, further comprising the administration of an anti-cancer drug.

6. The method of claim 5, wherein the anti-cancer drug comprises cisplatin, gefitinib, gemcitabine, pemetrexed or a combination thereof.

7. The method of claim 1, wherein the human NSCLC has KRAS mutation.

8. The method of claim 1, wherein the human NSCLC has KRAS wild type.

9. The method of claim 1, wherein the human NSCLC is resistant to gefitinib, erlotinib, cetuximab, matuzumab, or panitumumab.

10. The method of claim 1, wherein the (S)-thioridazine or a pharmaceutically acceptable salt thereof is administered to the subject in need to minimize risks of catalepsy.

* * * * *